US008532959B2

(12) United States Patent
Gopalan

(10) Patent No.: US 8,532,959 B2
(45) Date of Patent: Sep. 10, 2013

(54) METHODS AND SYSTEMS FOR HIGH CONFIDENCE UTILIZATION OF DATASETS

(75) Inventor: Suresh Gopalan, Lexington, MA (US)

(73) Assignee: ReSurfX, Inc., Lexington, MA (US)

( * ) Notice: Subject to any disclaimer, the term of this patent is extended or adjusted under 35 U.S.C. 154(b) by 0 days.

(21) Appl. No.: 13/279,804

(22) Filed: Oct. 24, 2011

(65) Prior Publication Data

US 2012/0095695 A1    Apr. 19, 2012

Related U.S. Application Data

(62) Division of application No. 12/355,195, filed on Jan. 16, 2009, now Pat. No. 8,069,014, which is a division of application No. 11/497,926, filed on Aug. 2, 2006, now Pat. No. 7,480,593.

(60) Provisional application No. 60/705,083, filed on Aug. 3, 2005, provisional application No. 60/705,589, filed on Aug. 4, 2005.

(51) Int. Cl.
G06F 11/30    (2006.01)
G21C 17/00    (2006.01)

(52) U.S. Cl.
USPC .......................................................... 702/182

(58) Field of Classification Search
USPC .................................................. 702/183, 182
See application file for complete search history.

(56) References Cited

U.S. PATENT DOCUMENTS

| | | | |
|---|---|---|---|
| 5,991,752 A * | 11/1999 | Fukuda et al. .......................... 1/1 |
| 6,205,236 B1 | 3/2001 | Rogers et al. |
| 6,389,157 B2 | 5/2002 | Rogers et al. |
| 7,480,593 B2 * | 1/2009 | Gopalan ....................... 702/183 |
| 8,069,014 B2 * | 11/2011 | Gopalan ....................... 702/183 |
| 2002/0019706 A1 | 2/2002 | Braun et al. |
| 2002/0081006 A1 * | 6/2002 | Rogers et al. .................. 382/128 |
| 2003/0148286 A1 | 8/2003 | Larose et al. |
| 2003/0207270 A1 * | 11/2003 | Kung et al. ....................... 435/6 |
| 2003/0216916 A1 | 11/2003 | Navratil et al. |
| 2003/0226098 A1 | 12/2003 | Weng |
| 2004/0033485 A1 | 2/2004 | Li et al. |
| 2004/0059520 A1 * | 3/2004 | Shams et al. .................... 702/19 |
| 2004/0248308 A1 | 12/2004 | Toh et al. |
| 2005/0027462 A1 * | 2/2005 | Goode et al. .................... 702/22 |
| 2005/0038839 A1 | 2/2005 | Ghosh et al. |
| 2009/0299646 A1 * | 12/2009 | Shams et al. .................... 702/19 |
| 2012/0095694 A1 * | 4/2012 | Gopalan ......................... 702/19 |

OTHER PUBLICATIONS

Supplementary European Search Report dated Jan. 25, 2010 from related European Patent Application No. 06789227.3 filed on Aug. 3, 2006.

(Continued)

Primary Examiner — Michael Nghiem
(74) Attorney, Agent, or Firm — Burns & Levinson LLP; Orlando Lopez

(57) ABSTRACT

Methods and systems for high-confidence utilization of datasets are disclosed. In one embodiment, the method includes selecting a metric for determining substantially optimal combination of true positives and false positives in a data set, applying an optimization technique, and obtaining, from the results of the optimization technique, a value for at least one optimization parameter, the value for at least one optimization parameter resulting in substantially optimal combination of true positives and false positives. A number of true positives and a number of false positives are a function of the one or more optimization parameters.

6 Claims, 22 Drawing Sheets

(56) References Cited

OTHER PUBLICATIONS

Gopalan, Suresh: "ResurfP: a response surface aided parametric test for identifying differentials in GeneChip based oligonucleotide array experiments." Genome Biology, Deposited Research Article 5:P14, [Online] 5, No. 11, Sep. 28, 2004 XP002562945.

Quackenbush, John: "Microarray data normalization and transformation." Nature Genetics Supplement, vol. 32, Dec. 2002, pp. 496-501, XP002562946.

Yang, Ivana V. et al.: "Within the fold: assessing differential expression measures and reproducibility in microarray assays." Genome Biology, vol. 3, No. 11, Oct. 24, 2002, pp. 0062.1-0062.13, XP002562947.

Baggerly, Keith A. et al.: Identifying Differentially Expressed Genes in cDNA microarray experiments. Journal of Computational Biology, vol. 8, No. 6, 2001, pp. 639-659, XP002562948.

Xaingqin, Cui et al.: "Statistical tests for differential expresson in cDNA microarray experiments." Genome Biology, Article 4:201, vol. 4, Mar. 17, 2003, XP002562949.

Khodarev, Nikolai N. et al.: "Receiver operating characteristic analysis: a general tool for DNA array data filtration and performance estimation." Genomics, vol. 81, No. 2, Feb. 2003, pp. 202-209, XP00256950.

Cold Spring Harbor Laboratory: "Plant Genomes: From Sequence to Phenome." Program of Meeting Plant Genomes: From Sequence to Phenome, Dec. 9-12, 2004, [Online] XP002569251.

Leung, Yuk Fai et al.: "Fundamentals of cDNA microarray data analysis." Trends in Genetics, vol. 19, No. 11, Nov. 2003, pp. 649-659, XP004469779.

Naef Felix et al.: "Empirical characterization of the expression ratio noise structure in high-density oligonucleotide arrays." Genome Biology, Article 3(4): Research0018, vol. 3, No. 4, Mar. 22, 2002, pp. research0018.1-research0, XP021021132.

\* cited by examiner

Response surface criteria for identifying differentials and parameter optimization - 2

METHODS AND SYSTEMS FOR HIGH CONFIDENCE UTILIZATION OF DATASETS

CROSS REFERENCE TO RELATED APPLICATIONS

This application is a divisional of U.S. patent application Ser. No. 12/355,195, entitled METHODS AND SYSTEMS FOR HIGH CONFIDENCE UTILIZATION OF DATASETS, filed on Jan. 16, 2009 now U.S Pat. No. 8,069,014, which is a divisional of U.S. patent application Ser. No. 11/497,926, filed Aug. 2, 2006 now U.S. Pat. No. 7,480,593, entitled METHODS AND SYSTEMS FOR HIGH CONFIDENCE UTILIZATION OF DATASETS, which in turn claims priority of U.S. Provisional Application Ser. No. 60/705,083, filed Aug. 3, 2005, entitled METHODS FOR HIGH CONFIDENCE UTILIZATION OF HIGH-THROUGHPUT DATASETS, and of U.S. Provisional Application Ser. No. 60/705,589, filed Aug. 4, 2005, entitled METHODS FOR HIGH CONFIDENCE UTILIZATION OF HIGH-THROUGHPUT DATASETS, all of which are incorporated by reference herein in their entirety.

BACKGROUND

The present teachings relate to methods and systems for high-confidence utilization of large-scale datasets.

The recent sequencing of large number of genomes including human and development of arraying and other high-throughput technologies has resulted in increasing utility of these advances to study organismal scale data (cells, tissues, organisms etc.). With these advances and increasing output of large-scale and high-throughput data has increased need for methods and systems to utilize the data with high confidence (i.e., reduce false discovery) to optimally allocate resources for further development of concepts, hypotheses, technologies and products. Many of these technologies have been developed in the last decade and their quality is constantly improving, and so are the tools to utilize the datasets and to further refine the technologies. Here a few concepts and tools are presented that satisfy some of the needs of the latter goals.

Many systems used in large-scale measurements of organismal/cellular state involves multiple independent measurements of each parameter (e.g., genes/transcripts/proteins etc.). Two common forms of this type of technology that are widely used are (i) GeneChip® (Affymetrix, CA), where each transcript of a genome is measured using multiple independent probes, with each probe having a corresponding mismatch probe to estimate cross-hybridization—the former called a perfect match (PM) probe and the latter mismatch probe (MM)—(well described in patents and literature; e.g. U.S. Pat. Nos. 6,551,784, 6,303,301) (ii) typical measures of mixtures of proteins as peptide fragments using several variations mass spectrometry (e.g., Washburn et. al., 2001 and many variations for direct and comparative applications). A variety of applications of this type of multiple independent measurements of each parameter are currently in use and can be envisaged. Due to well documented prior knowledge (in literature and in patents) and evolving applications, the use of the technologies and generation of the data are not described here.

Most biological experiments (due to limitations of biological and other resources) utilizing such high-throughput data generation systems are conducted with small number of replicates. When possible the resultant data is analyzed using statistical or mathematical principles (for example to detect differentials between datasets exploring different conditions) to increase the confidence of the downstream steps used. But, the small number of replicates significantly reduce the statistical power in the analyses. In principle, the utilization of the independent measures of each parameter should alleviate significant part of this problem (at least in terms of improving power with respect to technical aspects of all steps of the process—e.g., manufacturing, handling, hybridization etc.). In the utilization of multiple independent measures there is a need for an understanding of the system specific properties and the behavior of the different parameters used in such analyses with respect to each other. Conversely, understanding properties of such datasets would help design better measurement technologies.

Whether applied to datasets with design principles similar to above example (multiple measures of each parameter under each condition) or otherwise the datasets across different conditions and replications comparable should be available. This step in data analysis is usually termed normalization (in this document used to represent the step after pre-processing data for technological design and data-collection specific effects, e.g., background correction). A good normalization is prerequisite to all further analysis and interpretations of the data.

The above brief background outlines the need i.e., constantly evolving technology and newer algorithms being proposed and no uniform or consensus approach been accepted and even lesser methods are accepted and predictably useful in dealing with multiple independent measures of each parameter (without an intermediate processing into a unified model based summary) highlights the need for improvements that would satisfy the many emerging needs in efficient and productive utilization of the deluge of data being generated in life sciences and other fields, and sets the stage for one kind of dataset being part of the invention.

SUMMARY

In one embodiment, the method of the present teachings includes selecting a metric for determining substantially optimal combination of true positives and false positives in a data set, applying an optimization technique, and obtaining, from the results of the optimization technique, a value for at least one optimization parameter, the value for at least one optimization parameter resulting in substantially optimal combination of true positives and false positives. A number of true positives and a number of false positives is a function of the one or more optimization parameters.

The system behavior in terms of true and false positives is typically viewed as an appropriate response surface of the key parameters. In another embodiment, the method of the present teachings for summarizing parameter value includes grouping measurement result from a data set into a number of pairs of measurement results, determining, for each one pair of measurement results, whether predetermined measures for the one pair of measurement results satisfy threshold criteria, classifying a pair of measurement results from the number of pairs of measurement results as not changing if the predetermined measures do not satisfy the threshold criteria; comparing, if the predetermined measures satisfied the threshold criteria, one measurement result in each one pair of measurement results to another measurement result in each one pair of measurement results, classifying, after the comparison, each one pair of measurement results according to result of the comparison. selecting a common set of measurement results from the classified plurality of pairs of measurement result for use with the data set, and providing summary measures for a parameter utilizing the common set. Various embodiments that present parameter estimation methods, data normalization methods and methods for testing quality of analyses are disclosed. In addition, embodiments of systems and computer program products are also disclosed.

For a better understanding of the present invention, together with other and further needs thereof, reference is made to the accompanying drawings and detailed description and its scope will be pointed out in the appended claims.

DETAILED DESCRIPTION

Figure 1:
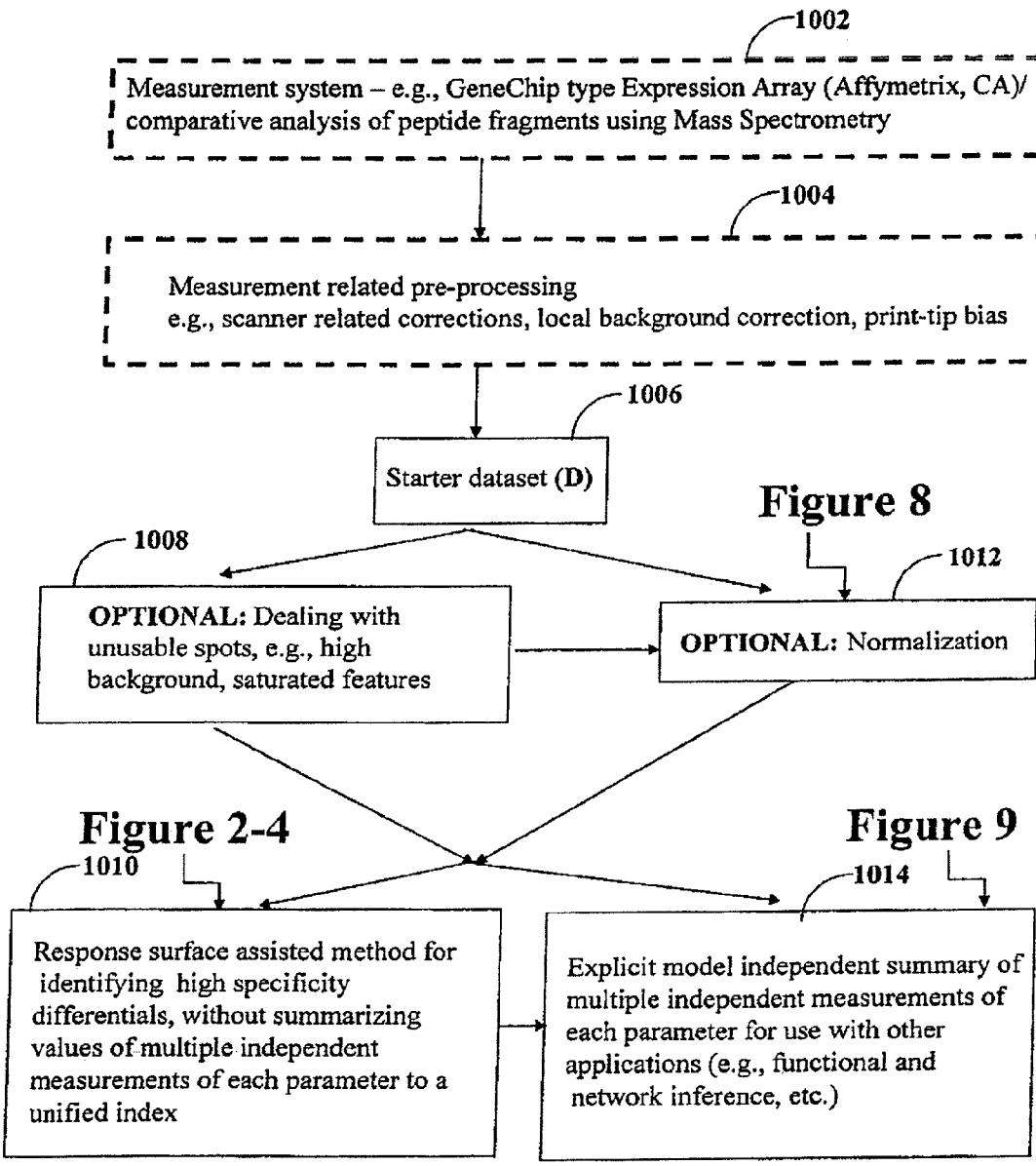
FIG. 1 depicts a flowchart representation of an embodiment of the method of the present teachings.

In one embodiment, the present teachings include a set of methods and algorithms to aid high-confidence utilization of large-scale datasets, viz., (a) a response surface assisted strategy to study datasets represented by multiple measurements of each parameter (especially using independent aspects of the same parameter) and aid in design of such measurement technologies and schemes, (b) methods for determining data-specific thresholds, (c) to test the efficacy of a selection strategy (statistical and/or mathematical) in the data analysis scheme, and (d) a new normalizing scheme for making datasets comparable.

Additional information on the data types being discussed and terminology used to describe these teachings is disclosed below.

While attempting to describe the teachings in generic scenario, the Affymetrix GeneChip® technology is used as example often, for convenience. Some design aspects of this technology would serve to highlight, but not limited to, the multiple measures type dataset discussed here. In the GeneChip® system each transcript is represented by eleven or more 25 nucleotide long probes complementary to the mRNA to probe the transcriptional status of the system being studied. A corresponding mismatch probe to represent the cross-hybridization signal (would be considered probe-specific noise) is included in the chip. High feature densities have been achieved and known and predicted transcripts have been arrayed onto one to few chips for human and other organisms. While the mismatch probes is included to represent the cross-hybridization or probe-specific noise signal and is used in that sense in examples described here, other variations (and applications) that do not include these MM probes (e.g., as suggested in dCHIP: www.dchip.org and Irizarry et. al. 2003) are equally well utilized by the approaches described as part of this set of teachings, and advantages if any would directly translate in the outcome.

Due to the physico-chemical properties of the probes and hybridization each probe though representing a single transcript (i.e., transcript expressed at a particular quantal level) has different hybridization intensity levels. This leads to difficulties in direct utilization of the signal levels. One common approach that has been extensively researched on and being continually developed is to use model based approaches to summarize the data represented by multiple probes into a single summary measure for each transcript (see U.S. Pat. No. 6,571,005, which is incorporated by reference herein). This approach has the advantage of user friendly representation of the data and in ease of utilization in advanced statistical and mathematical applications for the utilization of the data in the context of advancement of knowledge of the system/process being studied (using pattern recognition, classifiers for diagnostics, identification and study of pathways and new processes, lead candidates for product development etc.).

Some conventions used in this description are described herein below.

Throughout this text and in the accompanying figures the term parameter is used in two context specific manner: (i) to describe each experimental feature within a dataset (transcript, protein etc.,), and (ii) thresholds and other calculated numbers used in the process of utilizing the invention(s) in statistical and mathematical sense. In addition the difference between a calculated value and a set of calculated/estimated or designated threshold is differentiated by a superscripted single quote (for example distance designated d would be d' when used as threshold).

The use of term independent measures simply imply measures of one parameter (transcript etc.,) using entirely different measurement criteria (e.g., different regions of a transcript as probe, different regions of a protein—peptide fragments, more than one antibody to measure a protein etc.,—while the different region might have physical overlap it could have different signal properties under the same condition. This explicitly differentiates from the concept of statistical independence. Indeed some of the properties being studied, proposed and advanced here arise due to this difference. The embodiments described herein are not limited to this type of statistical independence.

Figure 14:
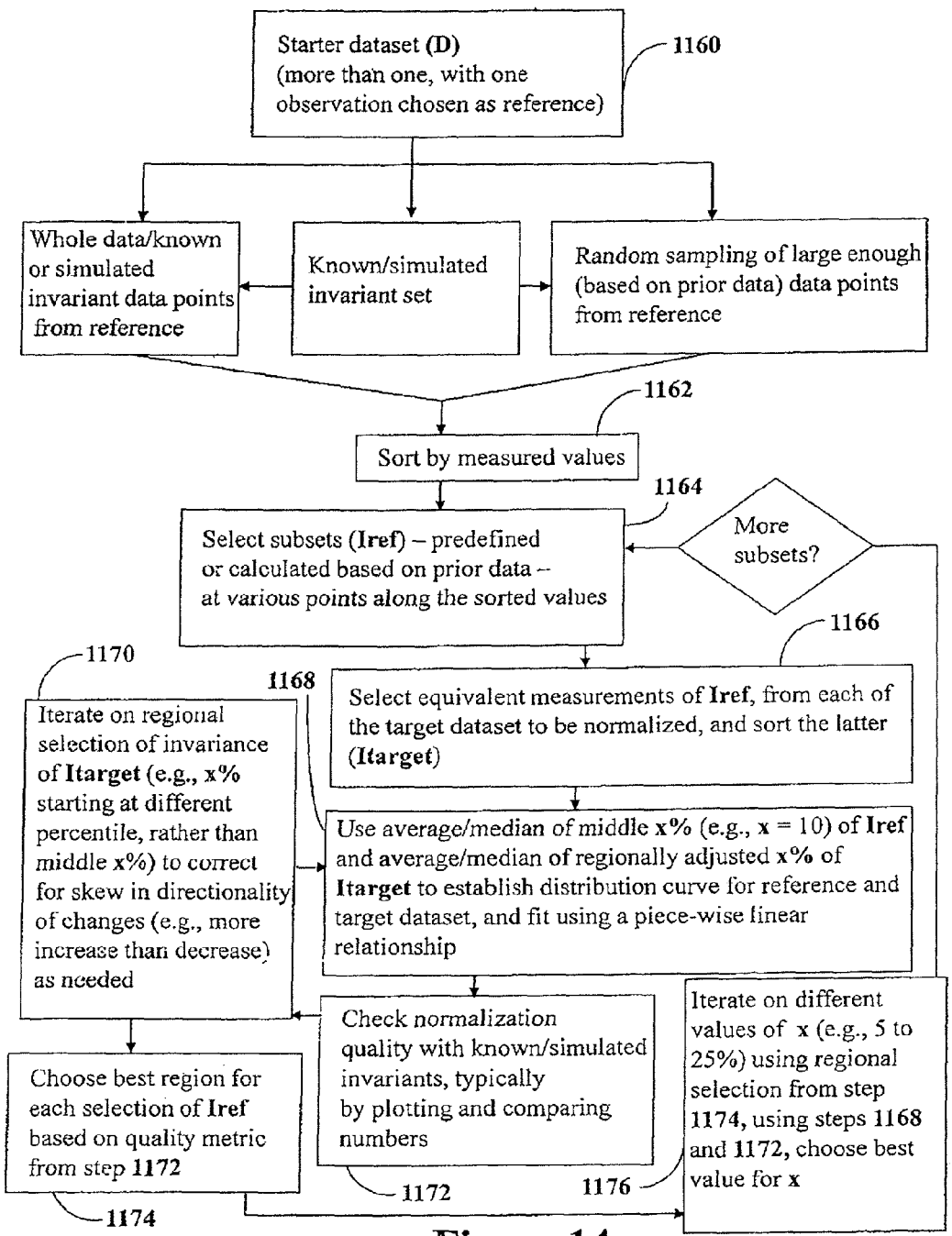
FIG. 14 depicts yet a further embodiment of the method of the present teachings in normalizing data.

An embodiment of the method of these teachings, a Response surface aided strategy (also referred to as ReSurfX) for the study of datasets is described herein below, where each parameter is measured using multiple independent measurements FIG. 1 illustrates one representative an embodiment of early stage workflow in processing data. In general data are collected from a measurement system step 1002 and pre-processed steps 1004 and 1008. This pre-processing would depend on the data-collection technology-specific properties and are assumed to be carried out, unless mentioned otherwise (if needed, prior to applying embodiments of the teachings described herein). Such pre-processed datasets are denoted as starter datasets and indicated by letter D step 1006 in the rest of the document and in the figures. Some other figures are referred to in this overview depicted in FIG. 1 (FIG. 2*a*- to FIG. 4 step 1010, FIG. 8 step 1012 and FIG. 9 step 1014). Aspects of FIG. 2*a* through FIG. 4 depict a response surface approach proposed to study the properties of a given data design that would (i) aid high-confidence data analysis, and (ii) conversely, aid development of design principles for a given system using some initial properties of the experimental and technological aspects. FIG. 14 depicts a new normalization scheme that is motivated by biological invariance principles. FIG. 9 depicts application of these two above embodiments in combination or using the first aspect alone, together with methods for data specific thresholds for parameters used in their application in a new summarization scheme as well as in high-confidence differential identification between datasets representing different observations of experimental or natural processes. Variations and details of some individual steps are referred to in those figures as additional figures with appropriate figure numbers. While many of the teachings presented herein relate to large scale datasets with multiple measures of each parameter in each observation set many individual steps such as normalization scheme, the equations used to optimize selection of true and false positives in comparative evaluations, methods for determining data-specific thresholds and evaluating the statistic or mathematical criteria used for identifying differentials are applicable to many other types of datasets that need not involve multiple measurements of each parameter.

Figure 2A:
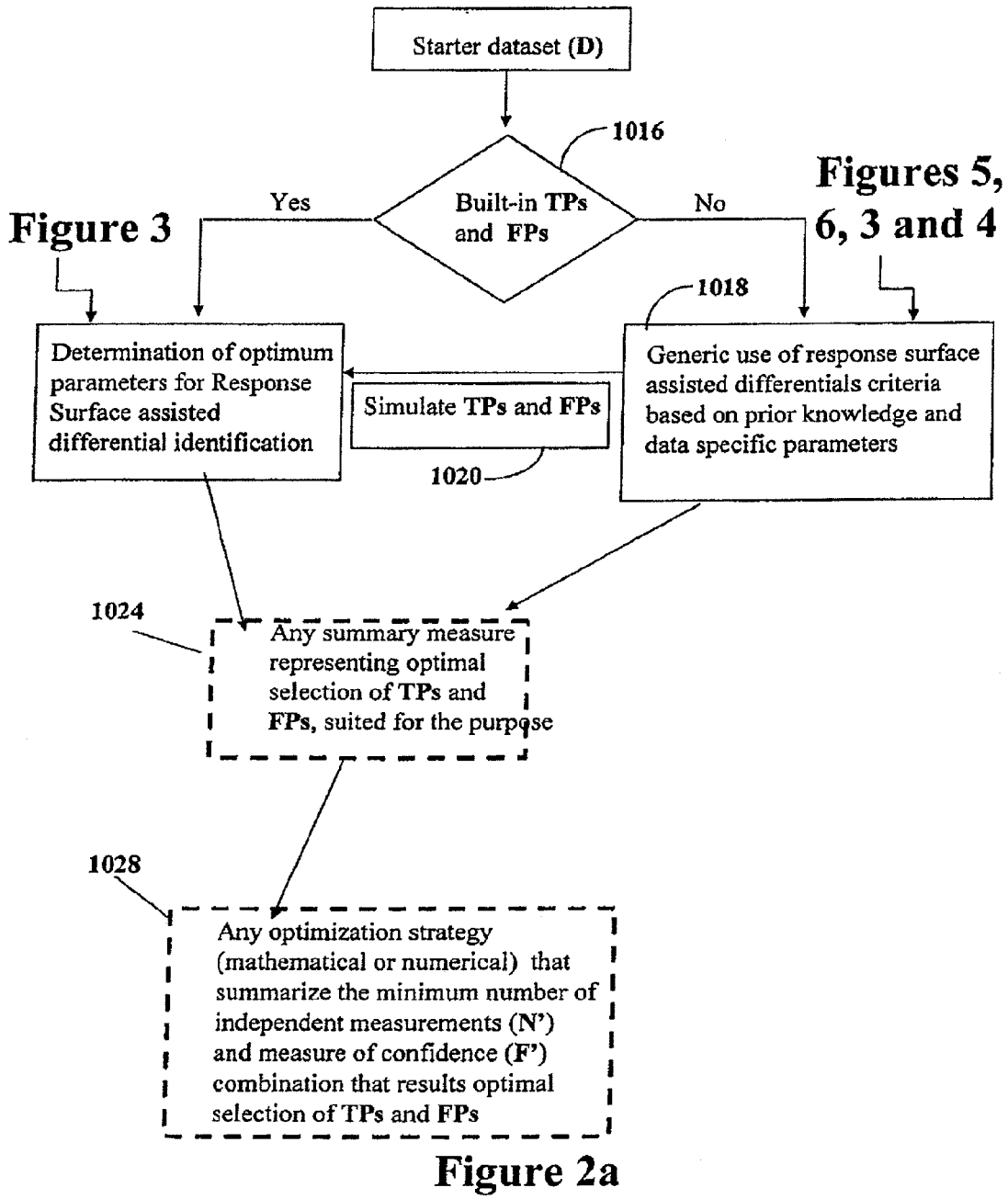
FIGS. 2a, 2b depict a flowchart representation of another embodiment of the method of the present teachings.
Figure 2B:
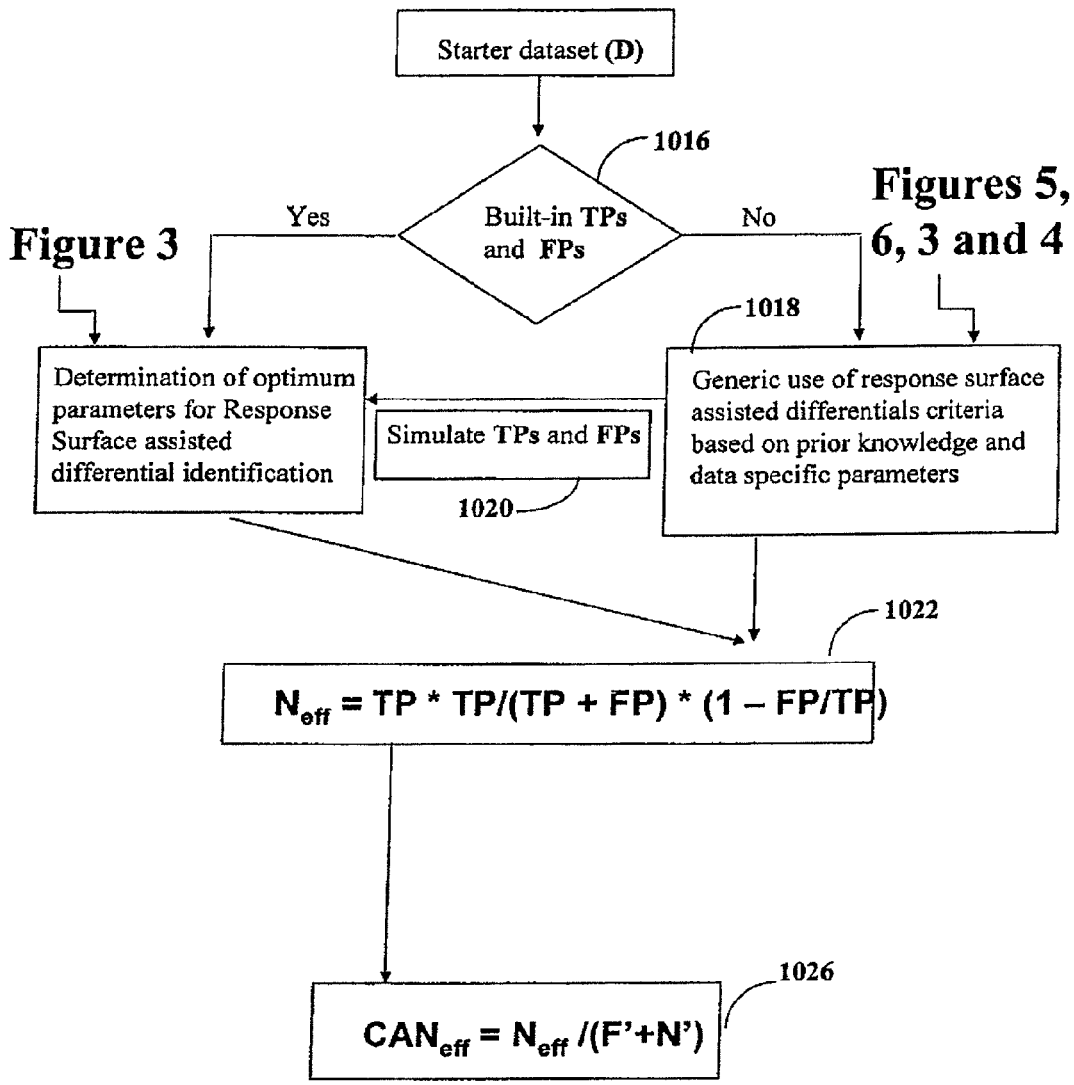

FIG. 2*a*, 2*b* show an embodiments of the method of these teachings. One instance has a tester system with built-in true and false positives mixed into the system, step 1016, or to mix an appropriately simulated true and false positives step 1020 (for example using techniques described in developing the methods and algorithms referred to as DaST and SCALEIT), described below. In one embodiment, the method of this teaching includes optimizing the identification of differentials between datasets maximizing the identification of true positives and minimizing the identification of false positives. In one instance, a metric termed $N_{\it eff}$ (for effective number of differentials) is utilized. In one embodiment, the following equation is utilized (also used in FIG. 2*b* step 1022)—alternative forms suited for specific applications can be used for this purpose (FIG. 2*a*, step 1024).

$$N_{\it eff}=TP*TP/(TP+FP)*(1-FP/TP)$$

Figure 16:
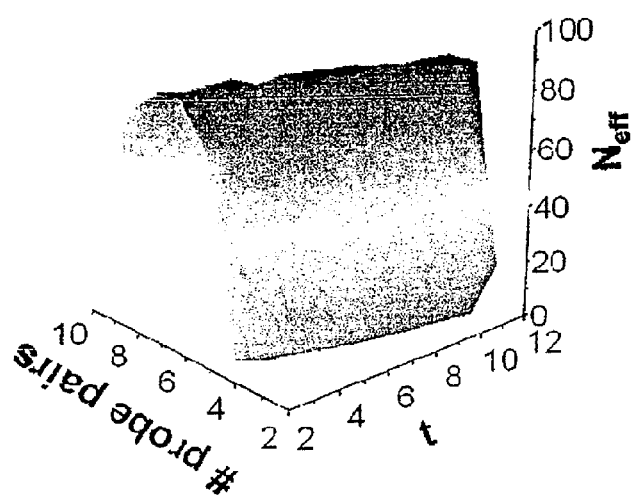
FIG. 16 depicts a graphical schematic representation of results from an embodiment of the method of the present teachings.

In one instance, a response surface of Neff with differing values of N (number of independent measures) of that parameter in that dataset included and any appropriate statistical/mathematical measure of confidence of the determination F (i.e., differential against the noise)—e.g., Student's t-test for pair-wise comparison of datasets (with replicates) or Fishers test for comparing multiple groups of data—is a surface with multiple maximum and minimum points on the surface. An example, these teachings not be limited to that example, is shown in FIG. 16 with GeneChip® datasets and pair-wise comparisons comparing known true positives (TPs) of two fold change and a large number of invariants (false positives-FPs) between datasets. In FIG. 16, the Dataset used is Affymetrix Latin Square Experiments (2 to 7) with three replicates each using U133A-TAG chip. The normalization used in the results shown in FIG. 16 was scaling average of all PM and MM intensity values between values 46,000 (saturation) and overall chip background (28) to 500. Intensity measure used in the results shown in FIG. 16 was PM—MM, for each probe pair. Parameters in the results shown in FIG. 16 are d'=B'=28; r'=1.1 (estimated for use as proof of principle for Response surface strategy). Statistic used in the results shown in FIG. 16 is Student's t-test (t used instead of abbreviation F' in text). AvgA and AvgB are used instead of max and min in FIG. 3*a*. Ranges used in the results shown in FIG. 16 are N (minimum number of informative probe pairs)=3-11, increments of 1 and at statistic of 3-10, in increments of 0.5; referred to as F and F' herein.

The response surface of $N_{\it eff}$ step 1022, in FIG. 16, indicates a broad range oft statistic and a range of N (independent measures included) that gives near maximal value of $N_{\it eff}$. In one embodiment, a cost factor involving N and F (symbol F is used as the measure of any statistic/mathematical measure of confidence used throughout the document) is defined. The lower the F and N that gives the substantially optimal combination of true and false positives, the better the ability to detect small changes with sensitivity. Increased specificity would result from the use of multiple independent measurements in its full form (i.e., without summarizing to a single value) in the analysis schema. It should also be noted at this stage that typically in analysis of large-scale datasets the problem of false positives is more rampant and less desirable than some loss in true positives (which by nature of experimental variability and small number of replicates would even be desirable in some instances). However, it should be noted that these teachings are not limited to the above described typical example. The equation below (also used in FIG. 2*b* step 1026) proposes one instance of a form of cost, the term CANeff for cost adjusted Neff), in terms of an additive factor of the statistic and the number of independent measurements included.

$$CAN_{\it eff}=N_{\it eff}/(F'+N')$$

As indicated in FIG. 2*a* (step 1028), other effective forms of cost may be possible and might be desirable in some instances. The calculation of F' (the statistical or mathematical confidence threshold) and N' are described in FIG. 3 and figures referenced therein. Use of a set of common N' measures for each parameter in all studies relating to a dataset or data from the same application (termed Chosenset—step 1122, FIG. 10) is described herein below. Typically, these teachings not being limited to the typical example, it has been observed that once the parameters for a technological platform has been calculated using well designed true and positives the same set of parameters seem to be applicable for other datasets from that technology (e.g., FIG. 3, step 1030). An alternative strategy that eliminates the need for iteration to determine F' as described above but determines a data specific threshold, is described in FIG. 6 and FIG. 7. In the embodiment shown in FIG. 6 and FIG. 7, substantially optimum parameters for F' and N' would still need to be determined based on knowledge based on test cases run using algorithm in FIGS. 3*a*, 3*b* starting step 1032 and FIGS. 2*a*, 2*b* steps 1026 and 1028.

Reverse application of the above described teaching would be to collect/simulate preliminary measures using multiple measures for each parameter (typically more than estimated need) in one or more likely scenarios of the use of that technology platform or a data collection strategy and based on calculated values of d', r' and F', and additionally using required confidence for that application, the optimal number of N (multiple independent measures) would be designed in the technology or the data collection strategy. An embodiment of the method for the devising of measurements includes obtaining a relationship between one or more preselected parameters and one or more performance indicators for the measurement of the data set, selecting a metric based on the at least one performance indicator, applying an optimization technique, and obtaining, from the results of the optimization technique, one or more substantially optimal values of the one or more parameters. The one or more substantially optimal values of the one or more parameters enables devising the measurement/collection strategy of the data set.

Figure 3A:
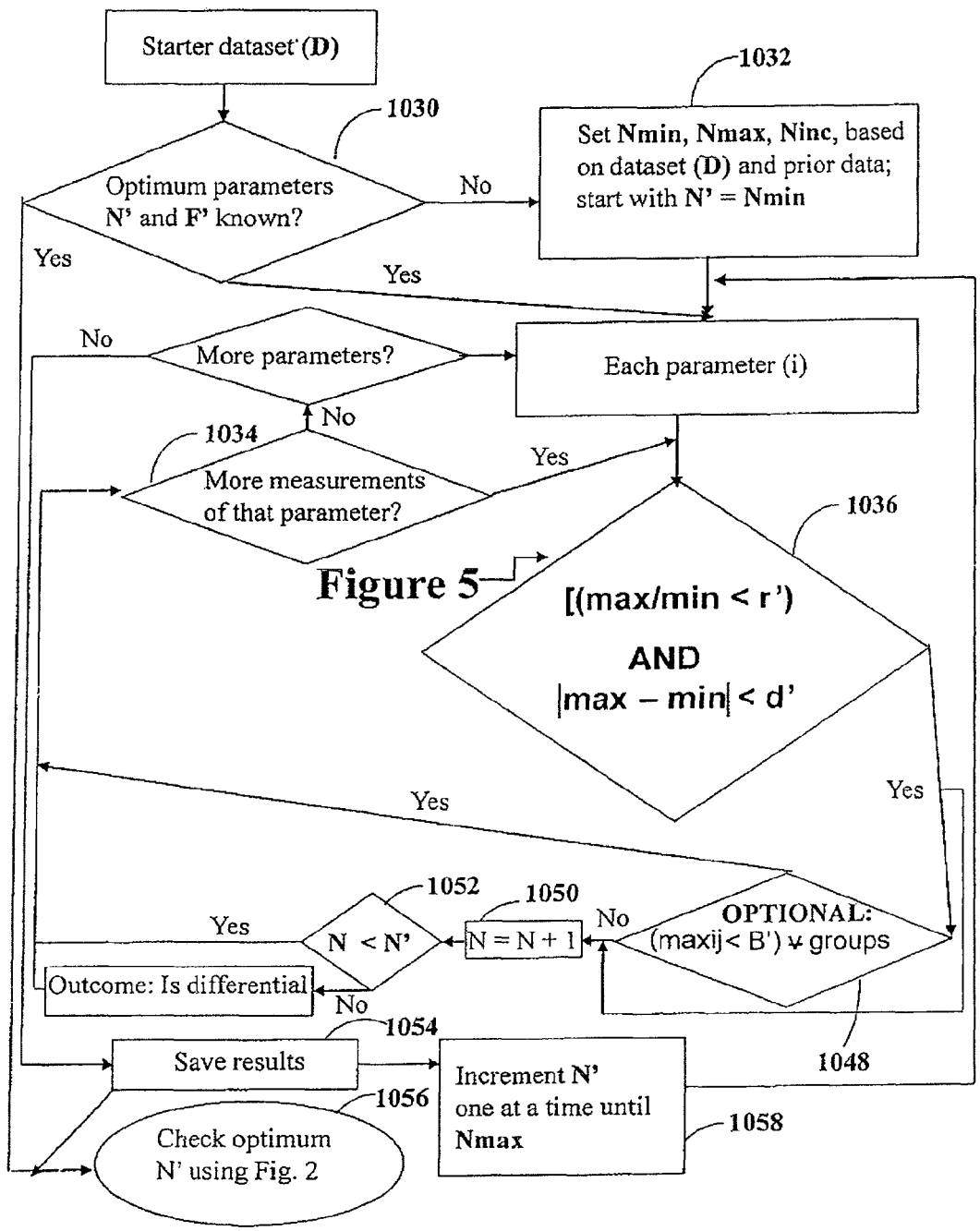
FIGS. 3a, 3b depicts a flowchart representation of the embodiment of the method of the present teachings shown in FIGS. 2a, 2b.
Figure 3B:
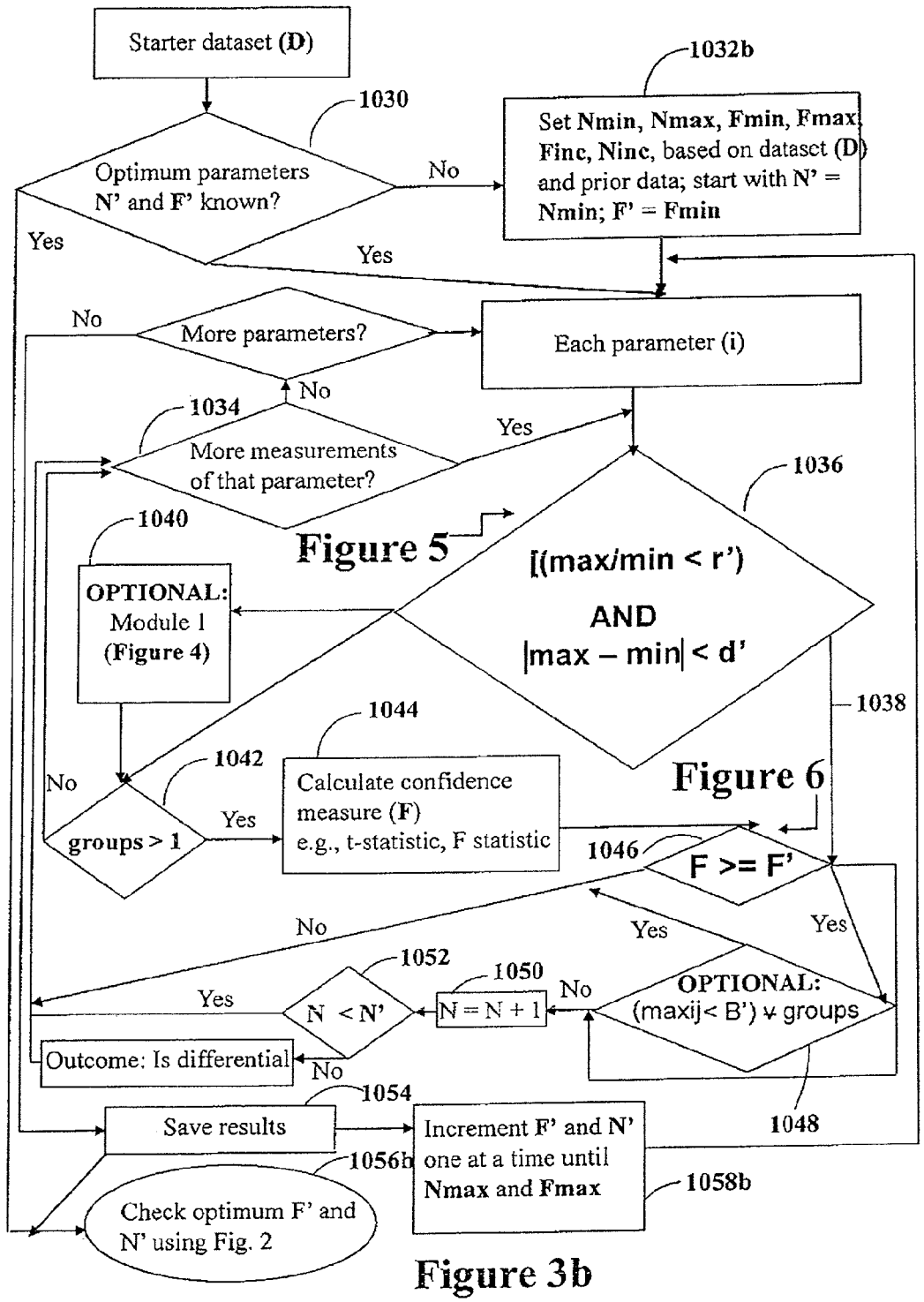

FIG. 3a and FIG. 3b depict an algorithm to study these behaviors and iteration over the parameters to determine the substantially optimal threshold. The method described in FIG. 3a and FIG. 3b includes iterating over possible values of N (number of independent measures included, steps 1032 and 1032b) and over a range of user determined confidence threshold of F (when there are more than one replicated group, FIG. 3b—step 1032b). The datasets could, in one instance, be composed of two or more observations, or groups of replicated dataset representing properties of different process states. The increment for iteration over N ($N_{inc}$) would be 1 (as this represents the number of measures), and for F ($F_{inc}$)—step 1032 and 1032b, FIG. 3a and FIG. 3b, respectively—would be determined by the user based on computational and other resources and the goals of the data analyses. Each parameter (i) is evaluated to satisfy a set of noise threshold criteria and confidence measures on a comparative basis (i.,e between two observations or between sets of replicated observations classified into groups) as described below. In one instance, only measures that satisfies the noise control criteria mentioned below and in FIG. 3a step 1036 and FIG. 3b step 1036 and step 1046 are used.

$$\left[\sum_{j=1}^{M} (x \mid F >= F', x_{jA}/x_{jB} >= r', |x_{jA} - x_{jB}| >= d')\right] >= N'$$

(It should be noted that other predetermined criteria are also within the scope of this teachings.) where $x_{jA}$ and $x_{jB}$ above refers to signal of that measure for that parameter being evaluated (x) between two conditions designated A and B, and j running over the M measures of that parameter i. F applies to cases with replicated groups in the dataset (step 1046). In FIG. 3a and FIG. 3b the terms max and min are used in step 1036 to represent a general case where max refers to maximum and min the minimum of the two values in case of single values being compared, maximum/minimum of two averages or medians or maximum/minimum of the group with the lower average or median. In all the examples used in the document to demonstrate the utility of these teachings, average is used when groups are being compared. Optionally, when all the data points of a measure j of that parameter being evaluated for differential are below a calculated or estimated overall background noise (B'—typically determined below which most data collected represent parameters below reliable detection threshold of that measurement system under the conditions used), they are eliminated from analysis step 1048. These thresholds (d', r' and B') avoid differentials in the noise range—this aspect is discussed in more detail in a future section. The algorithm for calculating dataset-specific thresholds on distance (d') and ratio (r') are described in FIG. 5. When the evaluation of a measure satisfy these criteria it is used in the measures included in the analysis (step 1050) and the next measure is evaluated. This is repeated for all the measures of a parameter (step 1034). When the number of measures passing the above criteria exceeds the threshold number of measures for that iteration (step 1052), then that parameter is considered differential between the observations (or groups) being compared. When all the parameters are evaluated the results are for that set of threshold used in that iteration are recorded (step 1054) and the values of the parameter thresholds are incremented and used for the next iteration (step 1058). Once the range of iterations are covered using the increments specified all the stored results are used to select the substantially optimal combination of N'- and F' in case of multiple replicated groups as in FIG. 3b—(step 1056), one embodiment of which is described in FIG. 2, using known or simulated differentials.

FIG. 3b, which is an extension of FIG. 3a deals with the case of multiple replicated groups involves optimization of two parameters, the number of measures of that parameter (N') and a confidence measure (F'). The use of the confidence measure based on replicated observations in combination with multiple measures substantially improves the comparative analyses of the data. In this case the iterations are carried out similar to that of FIG. 3a but for each increment of F in the range selected (i.e., F' for that iteration), the values as described in FIG. 3a above are calculated for the whole range of N through iterative loop with changing N' (steps 1032b and 1058b). The specifics of the strategy are nearly identical except that for each measure and for each evaluation cycle the confidence measure F (step 1044) that is calculated on a comparative basis between two replicates should also exceed the threshold F' (step 1046).

Figure 4:
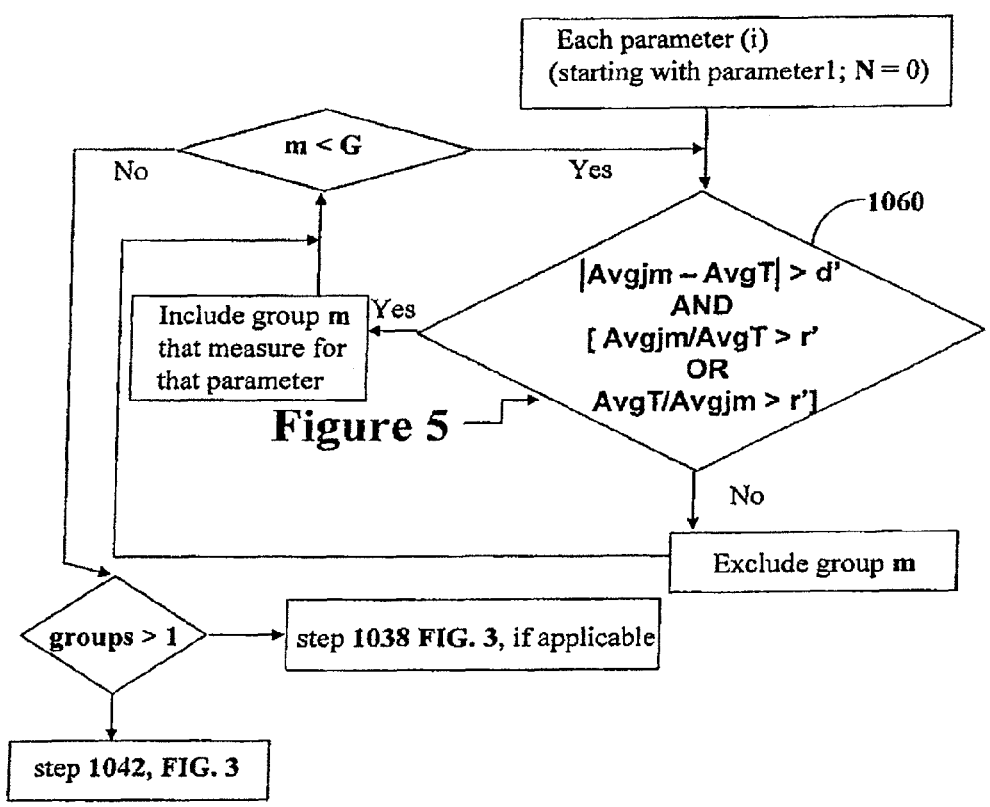
FIG. 4 depicts a flowchart representation of a section of the embodiment shown in FIG. 3a, 3b.

FIG. 4 (optional step 1040, FIG. 3b) depicts a strategy that eliminates some groups (in multi-group comparisons) based on these thresholding strategies and allows varying group number based differential identification for each measure to be evaluated. In this case the noise thresholding is based on comparison of average values over all G groups (termed AvgT step 1060) to that of individual group for each parameter i. As in the previous case average could be replaced by median or maximum and minimum of the groups or over all groups as described for FIG. 3.

Figure 17:
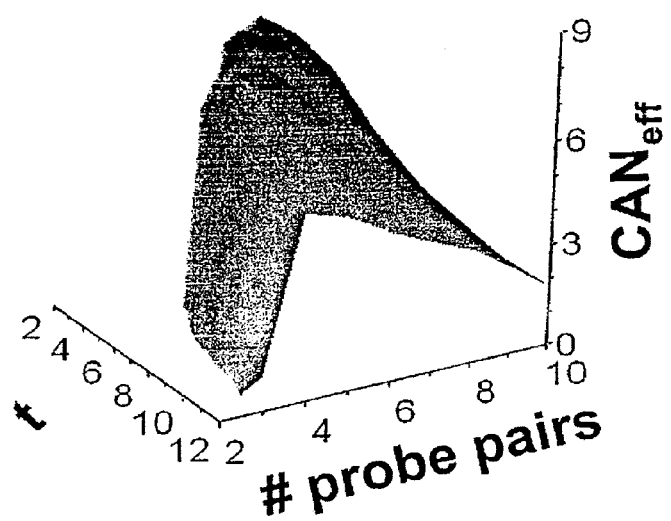
FIG. 17 depicts another graphical schematic representation of results from an embodiment of the method of the present teachings.

FIG. 17 depicts an example of the behavior of $CAN_{eff}$ with varying values of measurements included (N) and of the statistic (t-statistic in this case) for the same comparison shown in FIG. 16. It can be seen from FIG. 16 and Table 1 that (i) the nearly flat surface in FIG. 16 of the response surface of $N_{eff}$ can now be reduced to a few distinct peaks, and (ii) the statistical threshold is much lower than that of commonly used data analysis threshold for p value of 0.05.

TABLE 1

An example of the effect of different statistical threshold (F') and number of independent measurements used (N') on the true and false positives (of two fold change) identified

|  | 3, 6 | 3, 7 | 4, 6 | 4, 7 | 6, 6 | 7, 5 | 12, 6 | 7.71, 6 |
| --- | --- | --- | --- | --- | --- | --- | --- | --- |
| 0* | 1 | 0 | 0 | 0 | 0 | 0 | 0 | 0 |
| 0.125 | 4 | 1 | 3 | 1 | 3 | 3 | 1 | 2 |
| 0.25 | 3 | 1 | 3 | 1 | 1 | 1 | 1 | 1 |
| 0.5 | 1 | 1 | 1 | 1 | 1 | 1 | 0 | 1 |

TABLE 1-continued

An example of the effect of different statistical threshold (F') and number of independent measurements used (N') on the true and false positives (of two fold change) identified

|  | 3, 6 | 3, 7 | 4, 6 | 4, 7 | 6, 6 | 7, 5 | 12, 6 | 7.71, 6 |
|---|---|---|---|---|---|---|---|---|
| 1 | 5 | 5 | 5 | 5 | 5 | 5 | 4 | 4 |
| 2 | 7 | 6 | 6 | 6 | 6 | 6 | 5 | 6 |
| 4 | 8 | 8 | 8 | 8 | 8 | 8 | 6 | 8 |
| 8 | 8 | 8 | 8 | 7 | 7 | 8 | 7 | 7 |
| 16 | 8 | 8 | 8 | 8 | 8 | 8 | 8 | 8 |
| 32 | 9 | 9 | 9 | 9 | 9 | 9 | 9 | 9 |
| 64 | 9 | 9 | 9 | 9 | 9 | 9 | 9 | 9 |
| 128 | 9 | 9 | 9 | 9 | 9 | 9 | 9 | 9 |
| 256 | 9 | 8 | 8 | 8 | 8 | 8 | 6 | 8 |
| 512* | 9 | 9 | 9 | 9 | 9 | 9 | 9 | 9 |
| CR† | 5 | 4 | 5 | 4 | 4 | 5 | 3 | 4 |
| Total identified | 95 | 86 | 91 | 85 | 87 | 89 | 77 | 85 |
| Total present | 135 | 135 | 135 | 135 | 135 | 135 | 135 | 135 |
| FP | 16 | 2 | 5 | 0 | 0 | 1 | 0 | 0 |
| PPV | 0.86 | 0.98 | 0.95 | 1.00 | 1.00 | 0.99 | 1.00 | 1.00 |
| Sensitivity | 0.70 | 0.64 | 0.67 | 0.63 | 0.64 | 0.66 | 0.57 | 0.63 |

Indicated in Table 1 are the number of spike-ins of two fold difference identified at each threshold (out of 9, three in each comparison for three individual comparisons). The concentration of the spike-in (in pM) are indicated in the leftmost column in each case the concentration of the spike-in in the other dataset is twice this amount (except as indicated below). The threshold of t-statistic (F') and number of valid probe-pairs (N') is indicated in the first row as (F',N'). FP is number of false positives, PPV is positive prediction value [TP/(TP+FP)], sensitivity is [TP/(TP+FN)]. * 0 pM spike-in was compared to 0.125 pM spike-in, and 512 pM spike-in is compared to 0 pM spike-in. † CR indicates cross-reactive transcripts/probesets with homology to spike-ins (out of 9, three in each comparison for three individual comparisons). The dataset are the same as used in example shown in FIG. 16 and FIG. 17. (Note that, in FIG. 17, t used instead of F' above and that N' is equal to the number of probe pairs.)

Figure 5:
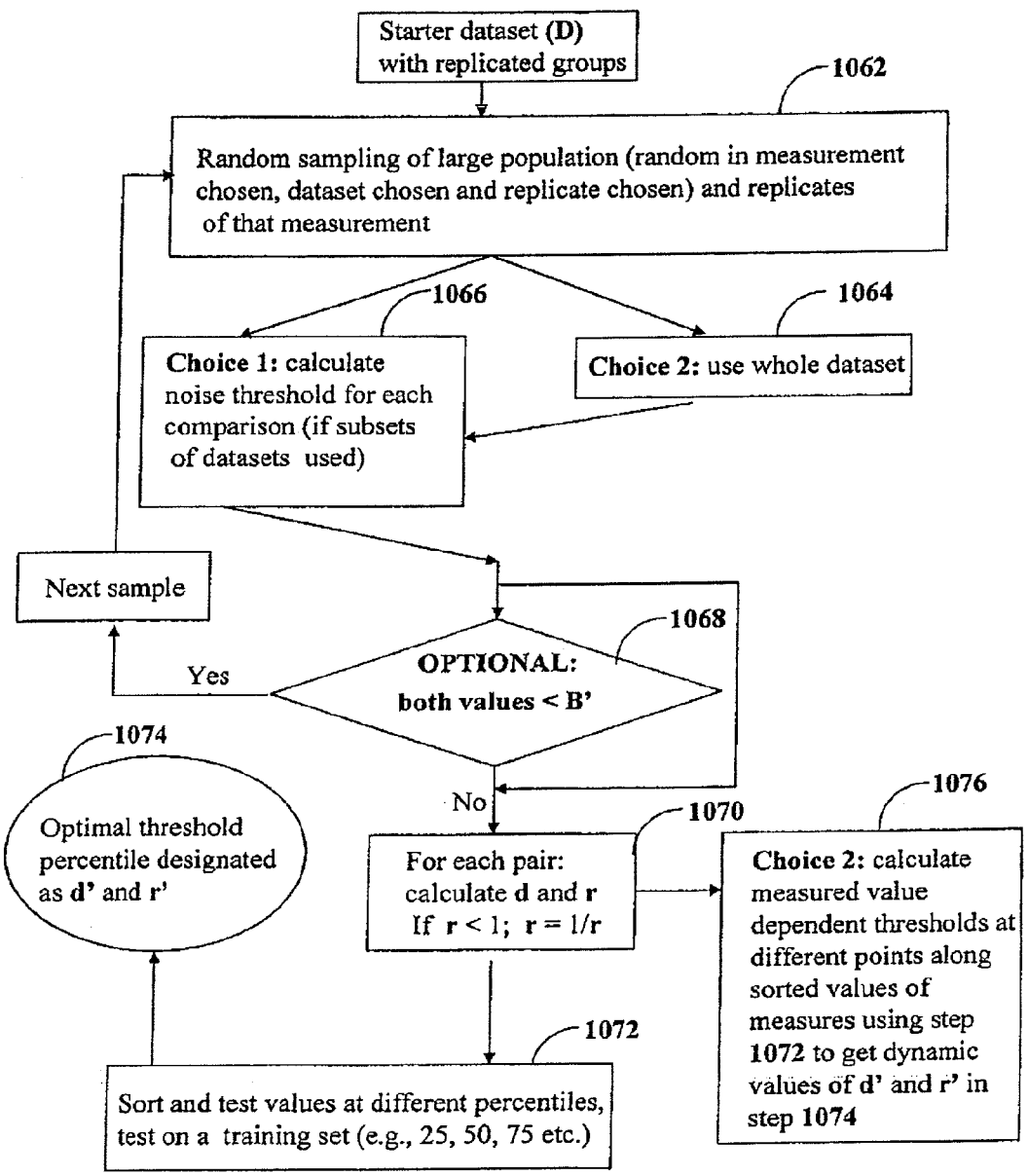
FIG. 5 depicts a flowchart representation of yet another embodiment of the method of the present teachings.
Figure 6:
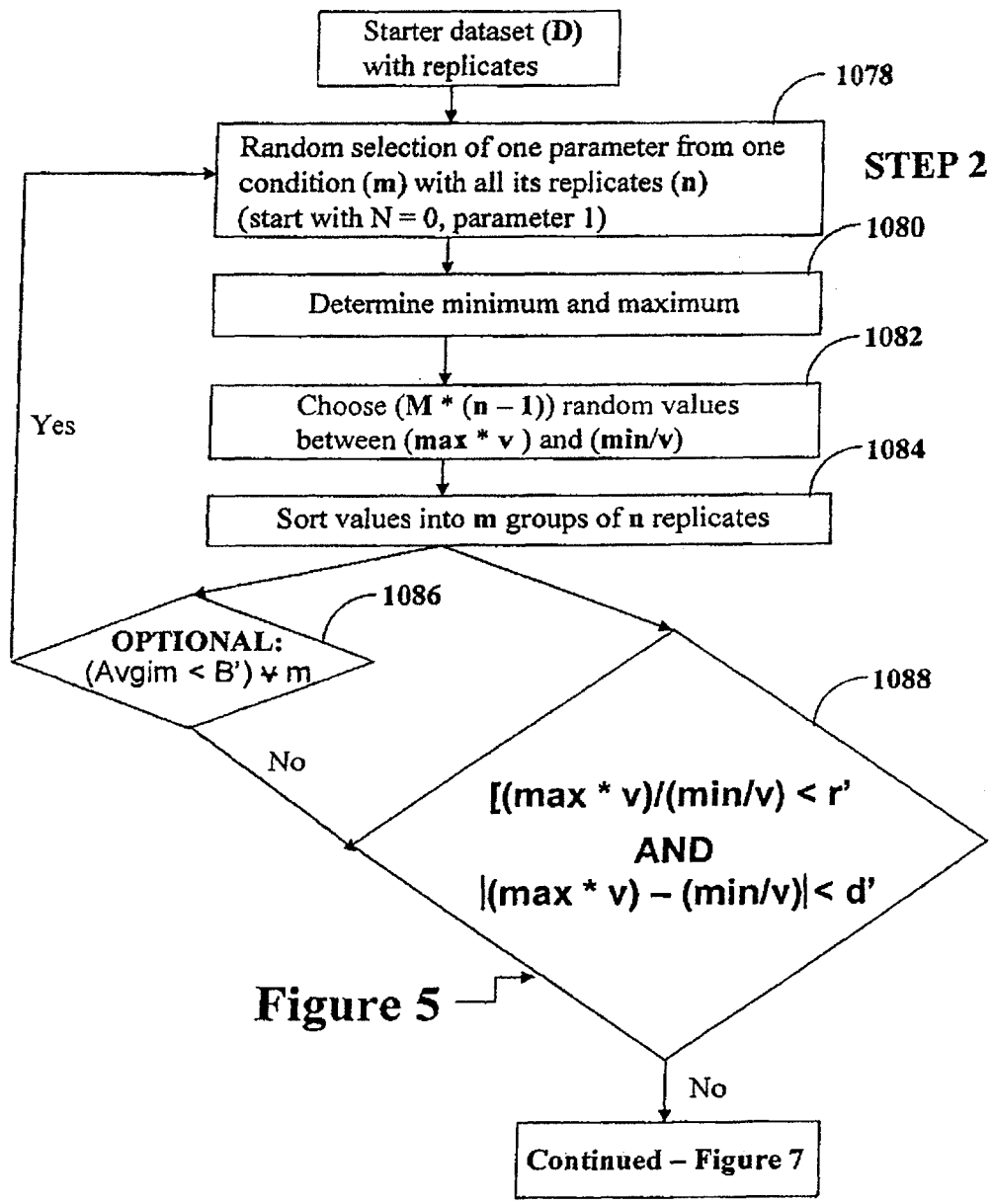
FIG. 6 and FIG. 7 depict a flowchart representation of a further embodiment of the method of the present teachings.
Figure 7:
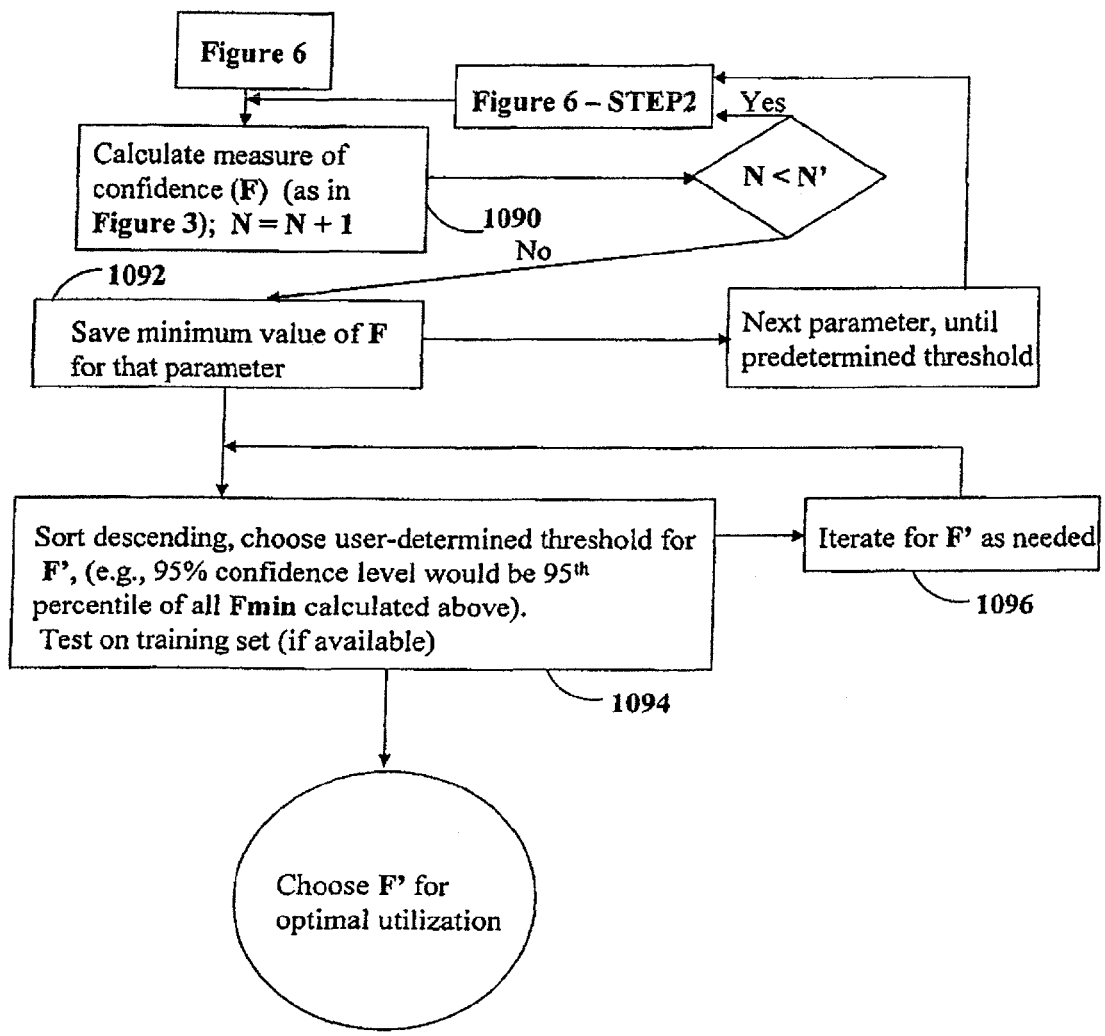

The example shown in Table 2 demonstrate the significant advantages of these findings, i.e., ability to select true positives without much impact on the number of false positives identified even at lower confidence thresholds. Further this precludes the need for guessing the threshold. Strategies for estimating data-specific thresholds are described later (FIG. 5, FIG. 6 and FIG. 7). Some aspects of applications of this invention in the context of gene expression measurements using GeneChip® technology are described in Gopalan, *Genome Biology* 2004 5:p 14, which is incorporated by reference herein.

TABLE 2

Application of data-scaling strategy (SCALEIT) to identify utility of the Response surface assisted strategy

|  | 1.5 | 2 | 3 | 4 |
|---|---|---|---|---|
| 3, 5 | 9287 | 13595 | 18001 | 19251 |
| 3, 6 | 8548 | 11031 | 15101 | 16657 |
| 4, 6 | 7553 | 12753 | 16947 | 18287 |
| 4, 7 | 6927 | 10333 | 13965 | 15431 |
| 6, 6 | 7418 | 11444 | 15235 | 16677 |
| 7, 5 | 8588 | 13500 | 17426 | 18690 |
| 12, 6 | 5164 | 8993 | 12204 | 13596 |
| 7.71, 6 | 6634 | 10584 | 14111 | 15600 |

Indicated in Table 2 are the number of probesets (average of three independent comparisons) detected (out of possible 22,301) at the given thresholds oft statistic cut-off (F') and minimum number of probe-pairs (N') satisfying this F', indicated as (F',N') in column 1. For the purpose of this evaluation three replicates were compared to three other independent replicates essentially representing the same samples scaled to the given differential (indicated in first row), and the values indicated are averages of three such independent evaluations. Again, the dataset used are the same as used in example shown in FIG. 16 and FIG. 17.

Embodiments of the method of this teachings which utilize (and are utilized in) the above described Response surface assisted thresholding strategy (ReSurfX) embodiment for identification of differentials using data-specific thresholds are described below.

Some of the embodiments described above utilized a dataset specifically designed for such purposes. Many currently existing datasets seldom are designed with built-in true and false positives, or not in sufficient number and variety. One embodiment, for the instance in which there is not a sufficient number of variety of true and false-positives utilizes a tester dataset as above to determine thresholds that could be used with that type of data generation technology. The use of distance and ratio thresholds have already been demonstrated in several conventional analyses schemes, but, in this teachings, algorithms for determining data-specific thresholds of these parameters are disclosed.

Embodiment for determining data-specific thresholds (DaST) of distance, ratio and statistic to avoid differentials in the noise range are disclosed herein below.

Different data collection platforms, pre-processing schemes (background correction, normalization etc.) and experimental systems have different levels of inherent and other handling based noise/variability (typically observed when comparing data between replicates).

FIG. 5 depicts a schema that determines data-specific thresholds for distance (d) (i.e., numerical difference between the two values or two groups) and ratio (r) that would typically lie within noise level for that data. In one embodiment, a percentile is determined at which these values d and r would be optimum based on the ability to detect substantially optimal combination of true and positives from a tester dataset, e.g., using $N_{eff}$ step 1022. For this purpose, a large enough random sampling of the data—step 1062 (or the whole data, step 1064) is selected and the distance and ratio are determined between the maximum and minimum for each selected measure for example within replicates (thus capturing the noise component of the data, step 1066). The calculated distances and ratios (individually) are sorted in ascending order of values (of d and r) and values of d and r at different percentiles on the ordered set of values are chosen as thresholds (d' and r')—step 1072—and used as described in applications described in previous sections or in determining thresholds for many data analyses scheme (either for selection or for elimination to avoid dealing with data just in noise range). The different thresholds are tested on a training set and optimum value chosen (for example by using equation for $N_{\it eff}$). This percentile value can be used to determine d' and r' (the selected thresholds—DaSTd' and DaSTr') step 1074. When additional specificity or safeguard is warranted scaled up versions of the determined values of d' and r', or a percentile threshold above that determined as optimum using the algorithm in FIG. 5 can be used to increase the confidence level. Dynamic thresholds can also be determined by using similar strategies on a data ranked by values of the measures at different points along the distribution and assuming piecewise linearity (step 1076).

FIG. 6 and FIG. 7 describes similar embodiments, but with additional intricacies for the determination of data-specific threshold of F (the measure of confidence used) to avoid differentials primarily within the range of noise (hence few true positives in those ranges). In this instance, a large enough sample of parameters and all its replicates are used and additional values within the range of values represented by the replicates are simulated, step 1080. As warranted, this range can be scaled up by a factor, termed vibrate factor—v (e.g., v=r', would imply find enough number of random values between r' times the maximum value and (1/r') times the minimum value)—step 1082. Using just the maximum and minimum value as range would be equivalent to using a vibrate factor of 1.0. The values for that parameter and the random values within (inclusive of the end points) are sorted to form enough groups, step 1084, with appropriate number of replicates and the measure of confidence calculated, step 1090. In case of multiple independent measurements of the parameter, as is the main theme of this section, this process is repeated N' (threshold number of measurements) times and minimum value is stored as one value of the dataset to be used for determining the substantially optimal threshold step 1092. The collected minimum values are sorted descending and the value of F is chosen at a user determined confidence threshold, DaSTF' (e.g., 95% confidence level would be vale at $95^{th}$ percentile), step 1094. This value can either be chosen on user determined confidence level or iterated for using a training set, step 1096. The noise range elimination strategies described earlier steps 1036 and 1048 (steps 1086 and 1088 in this algorithm) could optionally included in calculating DaSTd', DaSTr' and DaSTF'. Alternate manifestations of step 1092 could include median or any other percentile of values calculated for the N' measures of each parameter, rather than the minimum over the N' values of F.

When informative N is greater than N' the statistical threshold can be relaxed (for more sensitive identification of differentials), using basic statistical principle of independence (viz., $p^{N'}=p_1^{N}$). As mentioned before these data types do not exactly satisfy statistical independence principle, but the advantage obtained through this adjustment does not seem to come at recognizable cost in cases tested.

The above embodiment has been applied to a published defined dataset (as an example, embodiments not to be limited to applications or datasets of type used in this example) with large number of differential and invariant parameters without iterating over range of N and F values as in example 1, with good success (FIG. 16), by using the strategies described in FIG. 5, FIG. 6 and FIG. 7 and applying the results to FIG. 4. For this purpose N' value was set as 50% of all probesets (independent measures) available, based on prior trials with data used in example results shown in Tables 1 and 2 (Table 3).

TABLE 3

Application of data-specific thresholding strategy (FIG. 5-FIG. 7), BINorm scheme (FIG. 14), and ReSurfX (FIG. 3) on a test dataset with large number of true and false positives.

| Chip type | Choe et. al., Design Dros Genome1 | ResurfX identified TPs | FPs |
|---|---|---|---|
| Total probesets used | 3919 | | |
| Total non-differential | 2588 | | |
| Total differential | 1331 | 937 | 73 |
| >=2 fold | 781 | 732 | |
| >=1.5 fold | 1129 | 921 | |
| <1.5 fold | 202 | 16 | |
| Total probesets not used | 10091 | | |

The dataset used is from Choe et. al., [*Genome Biology* (2005) 6:*R*16], which is incorporated by reference herein. The parameters used are B'=107 (calculated, data not shown)
i. d'=57 (FIG. 5, at 50th percentile)
ii. r'=1.162 (FIG. 5, at 50th percentile)
iii. N'=7 (estimated—prior art)
iv. F'=1.65 (t-statistic—FIG. 6)

Intensity measure used is PM—MM, for each probe pair. Normalization used is BINorm at 25% middle values in each subset using known spiked-in invariant set built-in the data. AvgA and AvgB are used instead of max and min in FIG. 3.

While both these applications are depicted for multiple independent measurements it has a broad utility even in datasets with each parameter represented by a single value. This can simply be achieved by setting N'=1 in both these cases.

Embodiments of the method of the present teachings for summarizing parameter value includes grouping measurement result from a data set into a number of pairs of measurement results, determining, for each one pair of measurement results, whether predetermined measures for the one pair of measurement results satisfy threshold criteria, classifying a pair of measurement results from the number of pairs of measurement results as not changing if the predetermined measures do not satisfy the threshold criteria; comparing, if the predetermined measures satisfied the threshold criteria, one measurement result in each one pair of measurement results to another measurement result in each one pair of measurement results, classifying, after the comparison, each one pair of measurement results according to result of the comparison. For replicated data sets, the embodiment includes the steps of averaging the measurement results over replications and grouping the averaged measurement results into a number of pairs of averaged measurement results. The method proceeds similar to the preceding embodiment, utilizing pairs of averaged measurement results instead of pairs of results. An embodiment of such method of these teachings, EMINE: An Explicit Model INdependent Expression measure, for summarizing parameter value when represented by multiple independent measures is disclosed below.

As described above, conventional summarized values for multiple independent measures are model based. While such conventionally used model based approaches have significant advantages they may not always be desirable for all datasets. As described above, use of all independent measures directly confers significant advantage of specificity when identifying differentials between datasets. But such methodology has to be adapted for use with other well established advanced statistical and mathematical methods of analysis for pattern recognition etc, especially when the dimensions classifying the observations and the interactions of interest in the dataset gets higher. And embodiment of a explicit model independent expression summary method is disclosed, where the computational and adaptation costs for using the multiple measures of each parameter does not outweigh the disadvantages.

Figure 8:
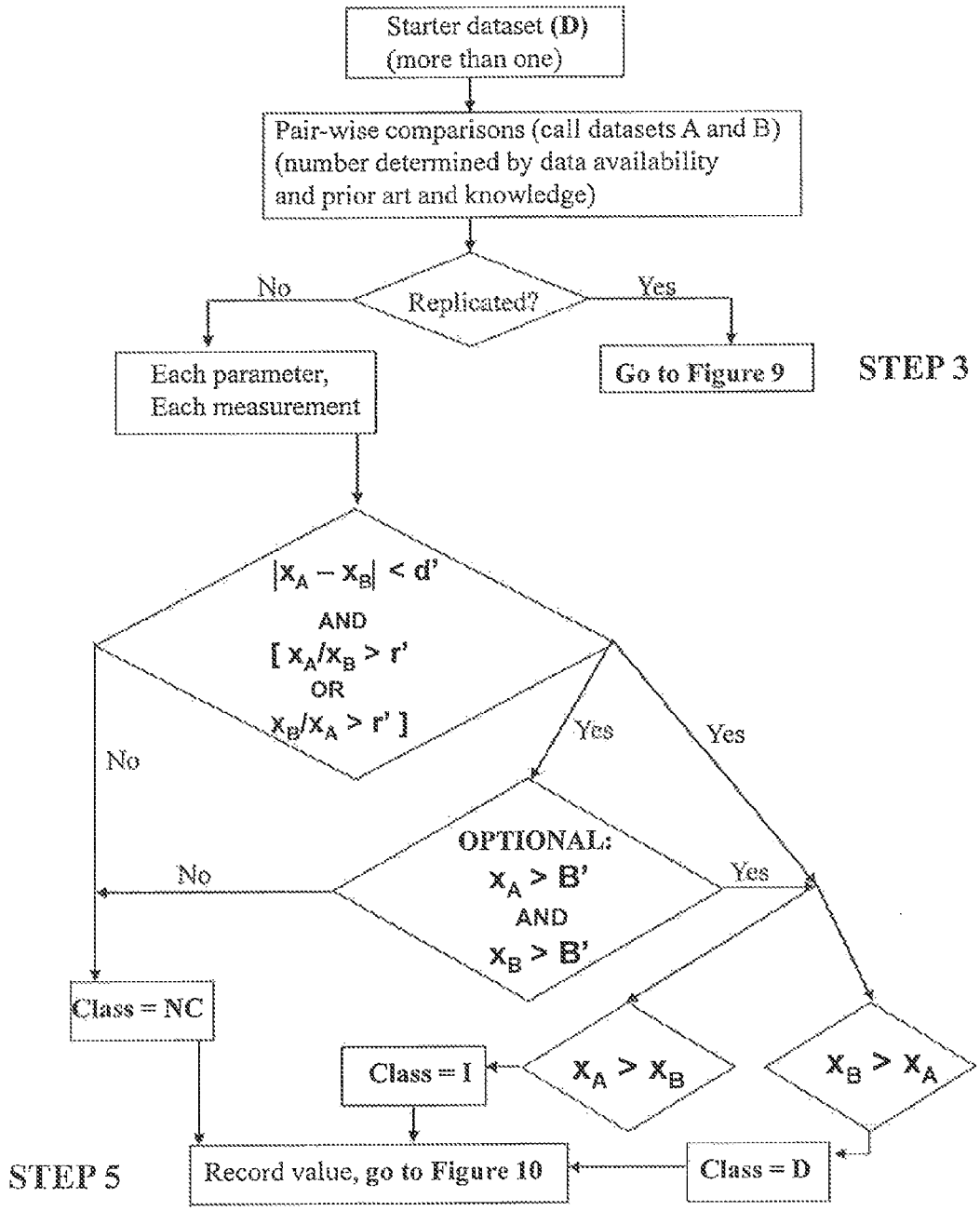
FIG. 8, FIG. 9 and FIG. 10 depict an embodiment of the method of the present teachings for expression summary.
Figure 9:
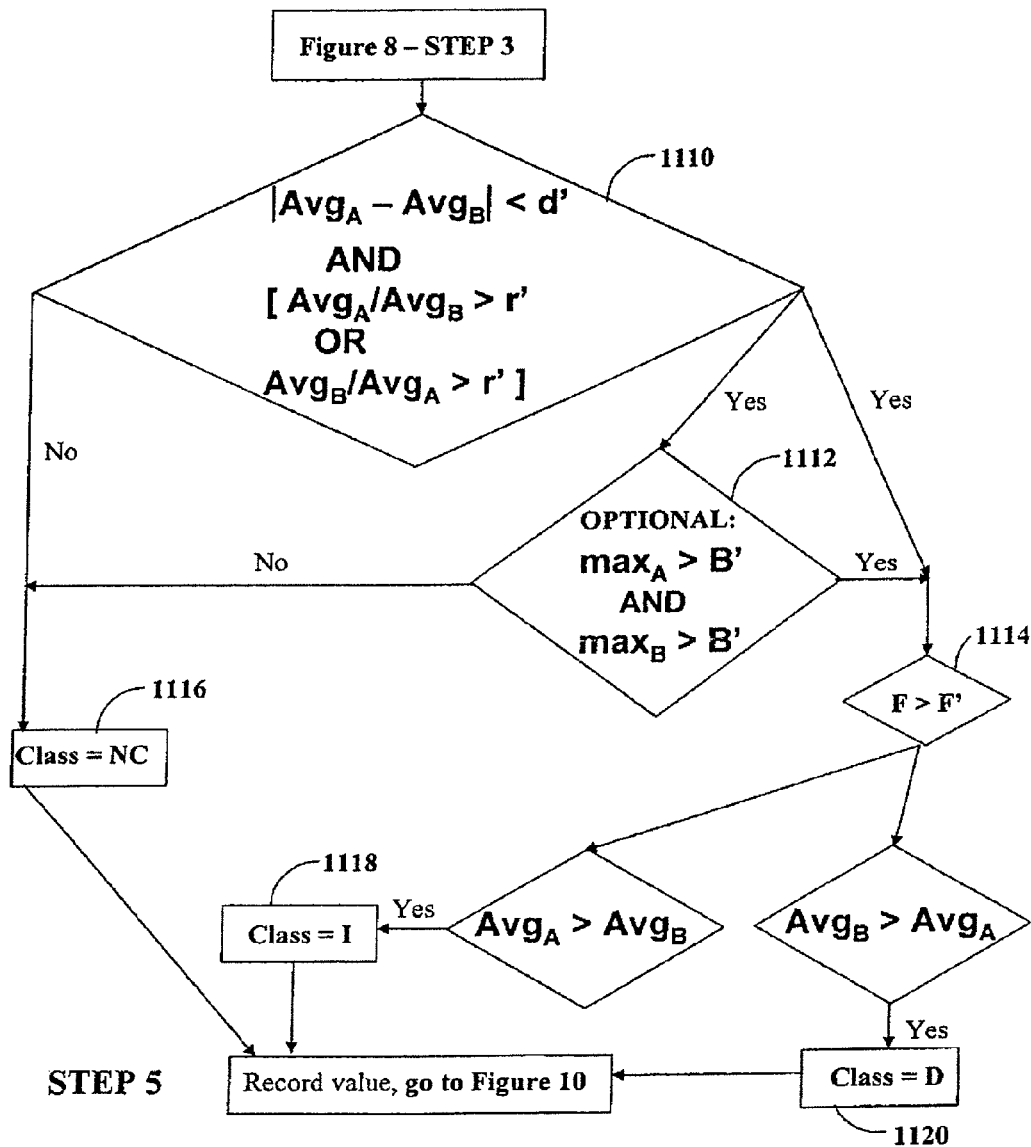
Figure 10:
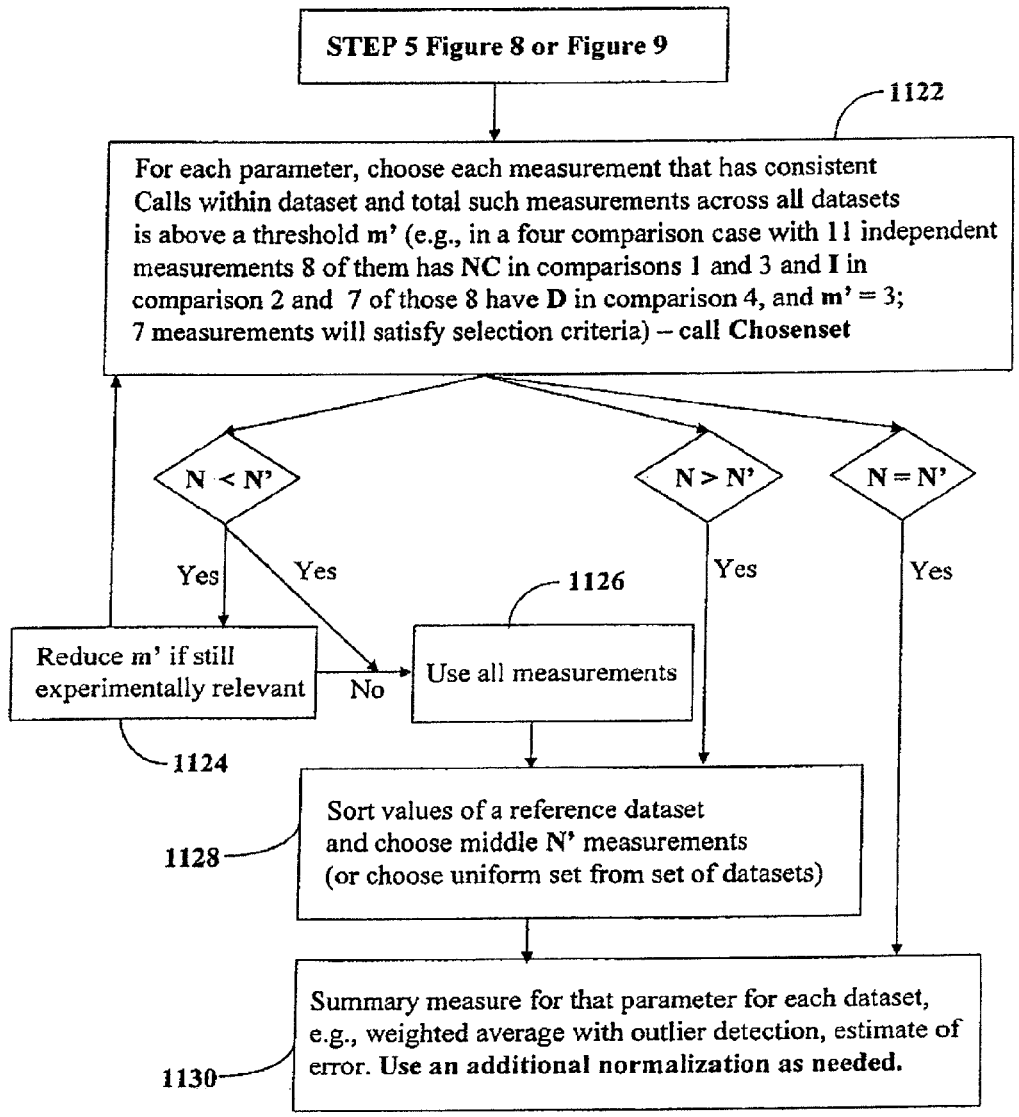

FIG. 9 and FIG. 10 describe an embodiment of the method of these teachings for summary measure using groups of data (typically replicates of observations in a dataset), while FIG. 8 and FIG. 10 describe a similar algorithm but for dealing with each observation as single unit (typically unreplicated observations). Each independent measure satisfying noise threshold criteria i.e., steps 1100, 1102, 1110, 1112 and 1114 (as in steps 1036 and 1048) of a parameter is classified as no change (NC), increase (I) or decrease (D) i.e., steps 1104, 1106, 1108, 1116, 1118, 1120 based on pair-wise comparisons, step 1098. Based on as many comparisons possible (or a minimum number of comparisons when large number of combinations are available) the independent measurements satisfying the specified criteria in the pairs over a particular threshold of datasets and as many independent measurements having uniform classification for that parameter are chosen for each parameter step 1122. When the number of independent measurements chosen for each parameter is above N' the values based one reference chip or a set of chips are ordered and the middle N' measurements are used for calculation of expression summaries for all datasets step 1128. Some alternate purpose/technology specific embodiments would include ordering the usable parameters N based on purpose specific criteria (e.g., along a predicted transcript and using a set that maximizes chances of detecting a variant of the transcript of interest among possible alternatively spliced forms). When the number of measurements chosen are below N' and the threshold on the number of pair-wise comparison could not be relaxed further without deterioration of quality (step 1124) all N measurements satisfying minimum criteria are used (step 1126), sorted and measurements representing middle N' values chosen. The expression summary could be a simple measure such as weighted average with outlier correction or any other established or modified summary measures step 1130. When a number of measurements are available such N' measurements that have uniform property over many comparisons (usually can be set as a threshold percentage of comparisons available to determine this property) a common set for use with that type of dataset for most uses beyond available or used for this step can be chosen and stored for future use. The use of such uniform set of measurements for each parameter for all datasets, termed the Chosenset step 1122, makes the summarized values have naturally better quality than using all or variable number of informative measurements. Use of an additional appropriate normalization after EMINE may be advantageous in some instances. One advantage of EMINE is the minimal use of numerical correction criteria.

In the context of biological applications, with the development of large scale dataset, a universal set of uniform measurements for EMINE can be devised and used. The strategy devised above can be interpreted as an approach to directly achieve this goal.

Embodiment of the method of these teachings for estimating fold change confidence estimates of differentials for Response surface based data analysis are disclosed herein below.

Figure 11:
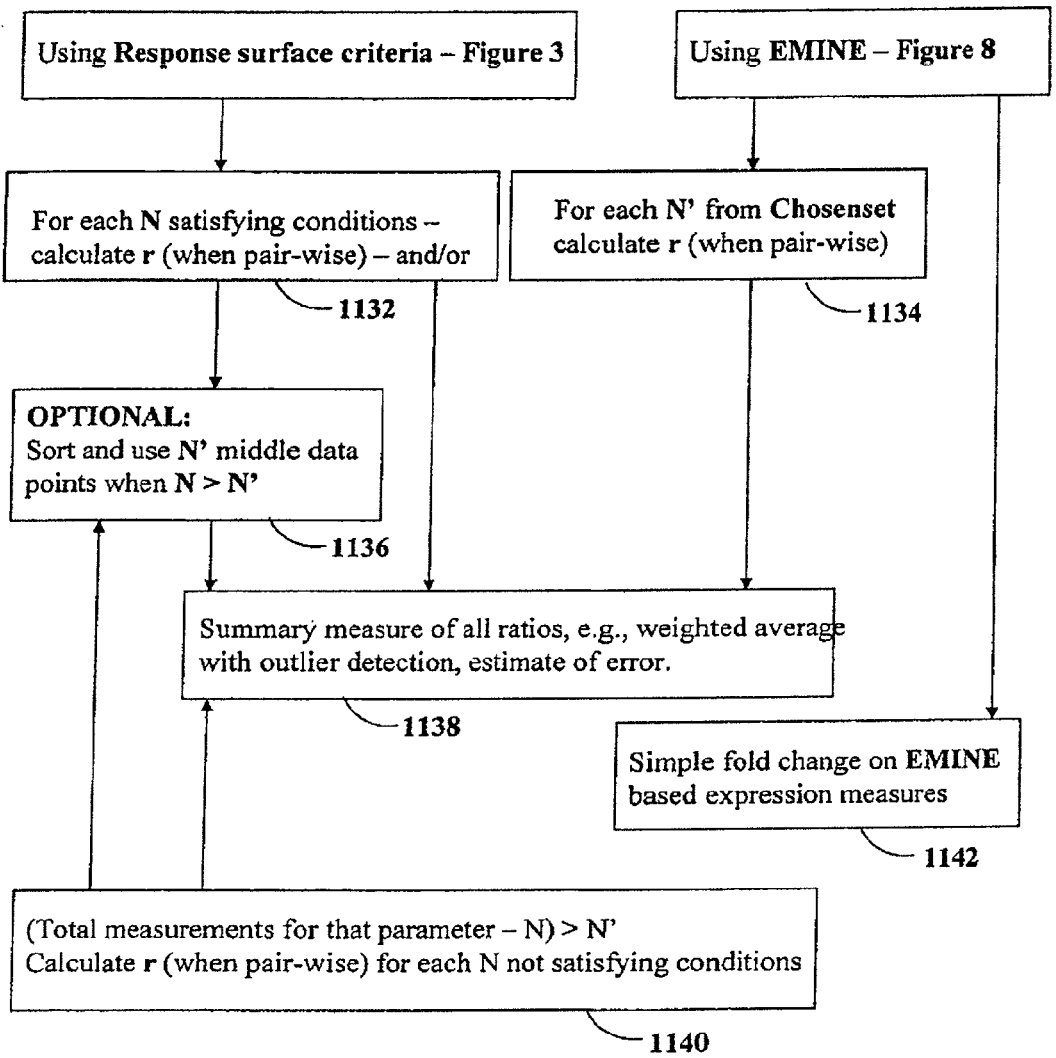
FIG. 11 depict another embodiment of the method of the present teachings to estimate fold change.
Figure 12:
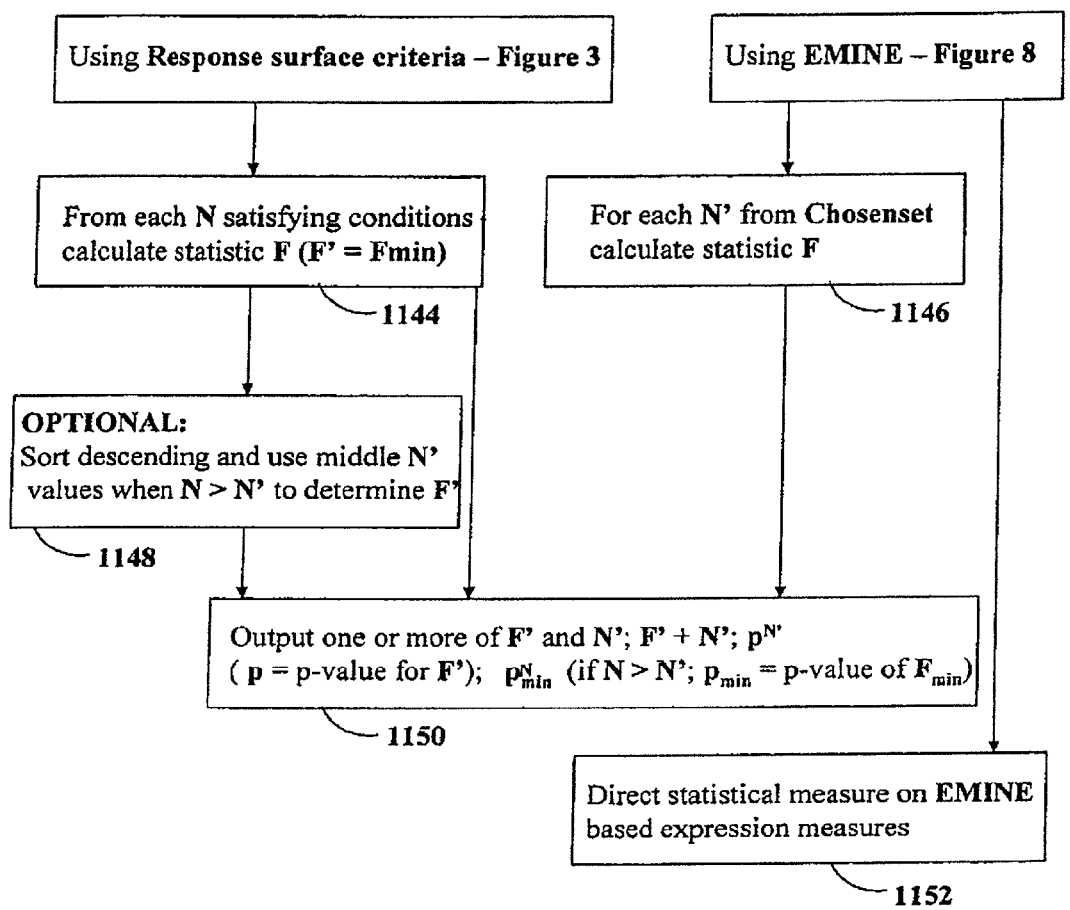
FIG. 12 depicts a further embodiment of the method of the present teachings to estimate confidence measure.

FIG. 11 and FIG. 12 depict embodiments for determining estimates of ratio of differential (in pair-wise comparisons) and estimate of confidence for differentials when using Response surface assisted strategy, respectively. In the simplest form estimate of ratio is obtained by taking pair-wise ratio for each selected measurement (selection is either based on noise threshold elimination strategies, step 1132) similar to steps 1036 and 1048, using all N passing threshold elimination, the Chosenset strategy (step 1134), or the N' values nearest to median (step 1136), as described below and in step 1042) of that parameter followed by a summary metric—step 1138—(e.g., weighted average with outlier correction as in step 1130). When N failing noise threshold elimination strategy is greater than N' (step 1140) the failed ones can be used for summary measure. When needed middle N' ratios as in step 1136 can be used. The spread of the estimated ratio for each parameter over the number of measures used is used to determine and report an estimate of the ratio. The measure of confidence uses similar techniques (steps 1144 and 1146) except that a minimum value is used to give the most conservative measure of confidence, other variations based on percentiles of all confidence measures from informative measurements of that parameter in that comparison could also be used. When informative N is greater than threshold N', an alternative is to use the middle N' values of a sorted (descending) array of F values—step 1148. The confidence measure can then be used as in the cost factor as an additive measure of N' and F' (step 1026) or can be converted to a p-value from a standard statistic or bootstrap based statistics and presented in desirable format (some usable forms are proposed in FIG. 12, step 1150). In the case of using EMINE summarized values, standard mathematical and/or statistical can be applied—steps 1142 and 1152.

An embodiment of a data-scaling method for testing efficacy of differential selection scheme used in analyses of datasets (referred to as SCALEIT) is disclosed herein below.

As has been used extensively in the above sections, a well designed tester dataset would be of extreme value in development and validation of algorithms used in various steps of the workflow. But, such well designed tester sets are seldom available that is appropriate for an experimental scenario, or some times limited by resources. Numerous data analysis schemes are used to glean useful information from datasets. Different schemes result in different degree of success (identifying true and false changes and relationships between parameters and/or different observations/conditions being studied). A simulation method that utilizes the variances structures present in the whole dataset to evaluate the efficacy of the data analysis scheme applied in a specific experimental situation is conceived, tested, and described below.

Figure 13:
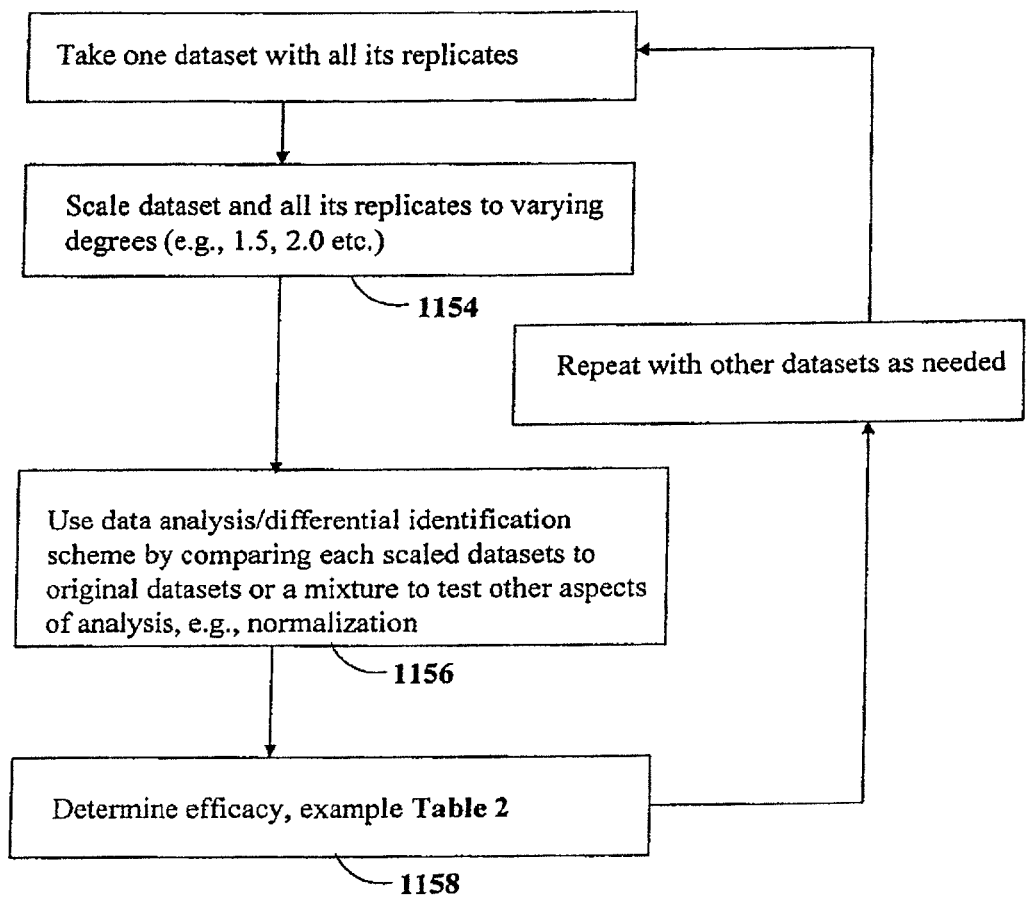
FIG. 13 depicts yet another embodiment of the method of the present teachings to test quality of data analyses tools used.

FIG. 13 describes an embodiment of the method of these teachings using a data-scaling approach (SCALEIT), and an example of its utility provided.

Briefly, this embodiment, SCALEIT, involves scaling the whole dataset and its replicates to varying extent (e.g., 1.2, 1.5, 2 times etc.,)—step 1154—and application of the data analysis/differential identification scheme—step 1156. The advantage with this approach being the utilization of all possible variance structures inherent to the system. An example of this approach in the context of Response surface assisted method to identify differentials at various thresholds—step 1158—is shown in Table 2. Some forms of data analysis schemes would be better tested by modifications of this unidirectional scaling strategy, for example bidirectional changes or mixture of such changes suitably combined with original dataset.

An embodiment of the method of these teachings for normalizing data from a data set includes the steps of sorting data from the data set according to measurement value, selecting, according to a predetermined criterion, reference subsets, the reference subsets having at least one reference measurement value, selecting, from the sorted data, data elements having measurement values substantially equivalent to the one or more reference measurement values, sorting the data elements having substantially equivalent measurement values, the sorted data elements comprising a sorted substantially equivalent subset, and utilizing the one or more reference measurement values and the sorted substantially equivalent subset to normalize the data set. An embodiment of such teachings motivated by principles of biological invariance to normalize data, referred to as BINorm, is disclosed herein below.

Array based as well as many other technologies rely highly on normalization (or some form of numerical equivalency of data) between datasets within a platform and across platforms. Most normalization used to date relies on ordering of datasets and correcting systematic variations in a intensity dependent manner either using the whole data based distributions, or in spatially separated groups as in print-tip normalizations (e.g., lowess). Invariably a rank based assumption is built-into the system including nearly exact distribution of datasets, or ordering the whole datasets and choosing rank based invariant sets between a reference and a target dataset (e.g. U.S. Pat. No. 6,571,005, which is incorporated by reference herein) or a more recently proposed variant of the latter method where the dataset is divided into ranges of expression values and invariant sets chosen by rank equivalence (U.S. Patent Application Pub. No. 200510038839A1, which is incorporated by reference herein). Example of other commonly used methods include extensive application of principles of variance distributions and attempts to reduce their systematic component using transformations or modeling). Improper use of normalization scheme can at times introduce artificial bias and error in datasets. An embodiment of the method of these teachings, which is motivated by fundamental behavior of biological systems, is disclosed below and shown in FIG. 14.

Frequently, in biological systems studying variation of all parameters in one or more experimental conditions there are always a proportion of randomly distributed invariant values in any given sample of the dataset. In addition in many systems the variation (or differentials) between experimental conditions and technical variations are random, bidirectional and randomly distributed. Such systems and systems with small number of real differences are amenable to this normalization scheme, termed, BINorm—to indicate biological invariance motivated normalization. This schema requires designation of one observation as reference—step 1160—and all other observations are normalized with reference to this dataset. Cyclical normalization, i.e., all against all in pair-wise manner might be of use in some instances.

The reference data is ordered by measured values—step 1162—and subsets are chosen along the total distribution of the data, termed Iref, step 1164. The measures equivalent to each subset (i.e., indexes of the data points in the subset are used) are chosen from the target data and this subset sorted, termed Itarget, step 1166. In its simplest form with the above stated assumption not significantly violated the middle x % of values in the target subset should have equivalent values of the subset from reference array—simplified version of step 1168—(e.g., middle 10% in a 100 point subset of Iref and Itarget). Thus the average (or median) of the x values in Itarget will be equivalent to Iref. The equivalence determined this way along the whole dataset would then be used to normalize using a piecewise linear functionality. The value of x would vary with the percentage of invariance and can be iterated upon, step 1176, after the above step or on another embodiment depicted in the picture after iterating on regional equivalence of values in Itarget as described below. As long as the percentage of invariance between the datasets is above x, there should be no degradation of quality even when much lower percentage, than actual invariance in the data is used. Variations in regional selection of invariance are needed when unidirectional skew in differentials is present between datasets. One embodiment to deal with such cases, represented in steps 1168 and 1170, is to iterate over the equivalent region by scaling the x % of ordered measurements of Itarget at different at different percentiles on the ordered data (e.g., x % starting at $10^{th}$ percentile rather then the middle) and scaling the value to the middle x % of Iref. A built-in training set, a large enough putative invariant set (see description below) can be used to test the quality of the normalization to particular datasets—step 1172—or using an appropriate test scheme for equivalence. Thus after iterating over the range of percentiles on ordered Itarget, the equivalent range chosen to scale the whole data would be the one that gives the best concordance between the two datasets as determined with the test using known/simulated invariants or another test scheme for equivalence—step 1174. BINorm scheme has the advantage of simple correction of systematic changes while preserving variability inherent in the experimental design, thus improving specificity and confidence in the utilization of resultant inferences from the analyses. An example of such usage with a perfect invariant set is shown in Table 3, though these teachings not being limited to such an example.

When data from multiple measurement platforms or variations in the measurement system of the same platform are used, a large enough presence of common link terms for the identifiers of the parameters should suffice to make the measurement values in between the datasets equivalent and comparable.

As mentioned above, the availability of large scale datasets for each organism and platform a large enough putative invariant parameters can be chosen and used for general purpose analyses of various kinds. While not all parameters may be truly invariant in all conditions being tested a majority should be useful. When most are not utilizable either the normalization scheme is not applicable to those datasets or that system is uniquely different.

It should also be noted that though this type of invariance is prevalent in biological systems, any experimental system or datasets having such properties are amenable to this normalization schema.

A system and computer program product that integrates the above described teachings to current databases and other software utilities is described below.

Figure 15:
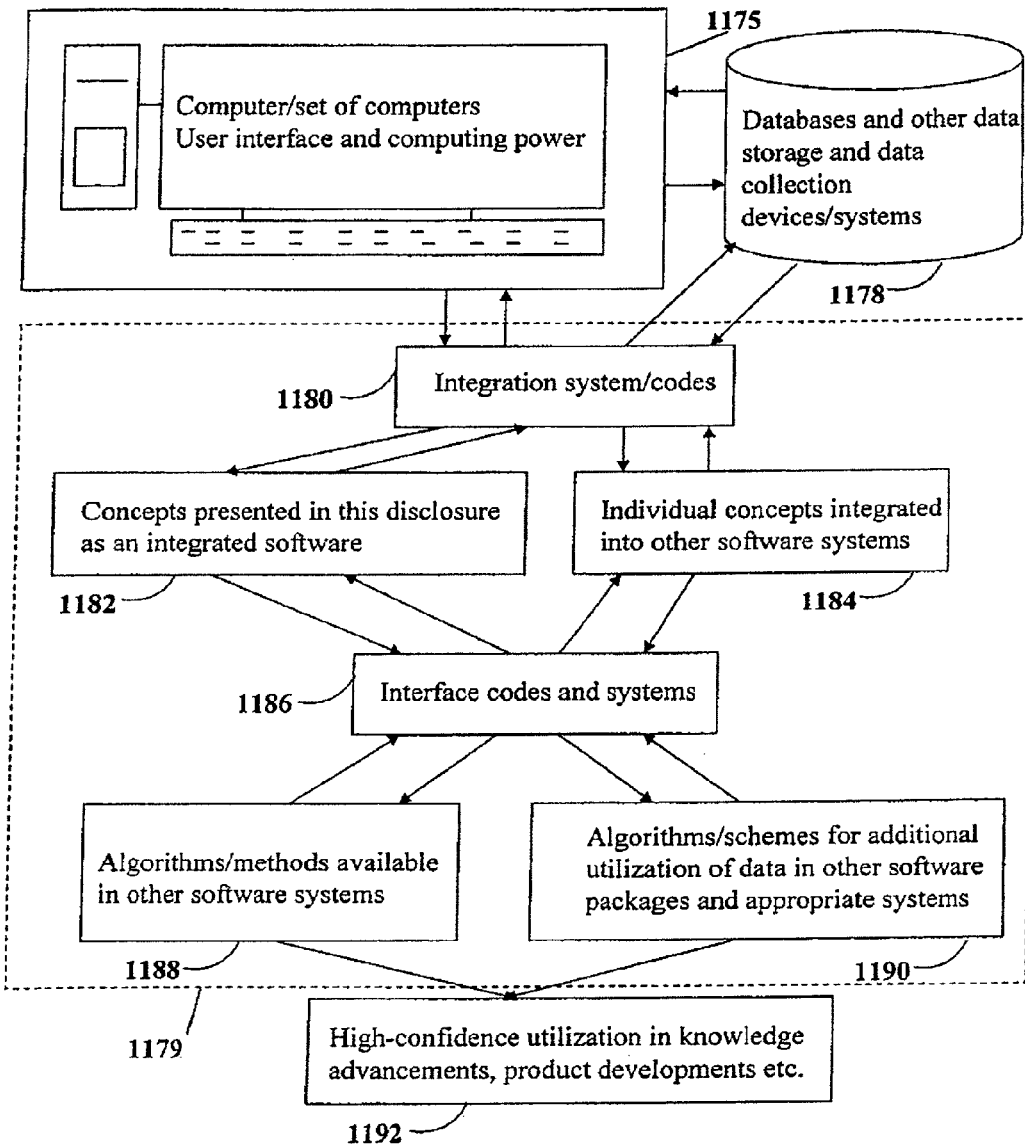
FIG. 15 depict an embodiment to develop a computer system to practice the present teachings.

As can be seen in the Figures and the above description, the teachings and concepts presented hereinabove are presented directly in the form of algorithms that are directly amenable to development of computer software—step 1182—(in any of the computer languages and user-interface tools) that can be integrated with databases and data warehouses—step 1178 and 1180—as well as ability to use output for other applications using other software or use as input methods/algorithms available in other software packages in conjunction with these teachings—step 1184, 1186, 1188 and 1190. A computer usable medium 1179 has computer readable code embodied therein, where the computer readable code is capable of causing the computer system 1175 to execute the methods of these teachings. Indeed, several of the teachings presented above were tested using software codes built in the C++ language. (However, the methods and systems of these teachings are not limited to any one computer language.) In addition these concepts individually can also be used as functions integrated inside other packages. A simple schema of an embodiment of a system of these teachings is presented in FIG. 15.

The teachings presented here have the advantage of minimal assumptions and numerical treatments in most cases thus adding to the goal of high confidence utilization of large-scale and many high-throughput data—step 1192. The concepts and algorithms for applicability for multiple independent measures of a parameter also would have applications in many other scenario (e.g., certain kinds of analysis of time course data, collection of meta-data as each parameter). While the utility are discussed in the context of high-throughput and large-scale organismal (or genome wide) data in biological contexts it should have utility in variety of other contexts where the possibility of application of the concepts and algorithms exist.

In order to better describe these teachings, the following exemplary embodiment, these teachings not limited to that embodiment, is presented below. The GeneChip expression data set used in these analyses is from the Affymetrix dataset released for purposes of algorithm development, and based on HG-U133A-Tag arrays Experiments 2 through 5, replicates R1 through R3. This data set was generated using a hybridization cocktail consisting of specific RNA spike-ins of known concentration mixed with total cRNA from HeLa cell line, by Affymetrix. All probesets starting with AFFX not part of the spike-ins of known concentration were removed for calculation of true and false positives involving spike-ins, since some of them had obviously discernible differences. Three probesets were reported to have perfect homology of 5 or more probe-pairs thus leaving 45 true positives and 22,185 false positives for each comparison in the dataset. Unless mentioned otherwise, values represented are based on average of three comparisons between experiments differing in spike-ins with two fold difference in concentration viz., experiments 2 with 3, 3 with 4 and 4 with 5. Probe level data were extracted from Cell files (using tiling coordinates defined by probesequence information supplied for the chip type—U133A-Tag by Affymetrix) and the mean of all signal values (of perfect matches and mismatches that were between the value 28 (the lowest background in the chips used) and a saturation value of 46,000) were scaled to target value of 500.

b is the background of that chip (as determined by Microarray Suite 5.0). When more than 11 probe-pairs represented a probeset only the first 11 (in their order of listing in Affymetrix probesequence file) were extracted and used. The difference between perfect match and mismatch value for each probe-pair was used for all further evaluations. Zero or negative differences were set to background.

The signal values were extracted using Microarray Suite 5.0 (Affymetrix, CA) with the trimmed mean (top and bottom 2% signal values are trimmed) for each array scaled to a target intensity of 500, for representation in FIG. 3. Standard definitions for sensitivity and positive prediction value (PPV) were used. Sensitivity was calculated as $sn=TP/(TP+FN)$; PPV was calculated as: $PPV=TP/(TP+FP)$, where TP is true positives, FP is false positives, and FN is false negatives. Typically, variance weighted average were used, as mentioned.

For the preliminary evaluation on biological replicates, the data from human patients with aortic stenosis (samples JB-as_0806, JB-as_1504 and JB-as_1805 were compared against JB-as_2111, JB-as_2604 and JB-as_2708, hybridized to U75-Av2 chips), from Genomics of Cardiovascular Development, Adaptation, and Remodeling site. NHLBI Program for Genomic Applications, Harvard Medical School. This chip consisted of 16 probe-pairs for most transcripts and the average background was used as 60. Calculations were performed using C++ on MS-Developer environment in Windows XP background.

Typical analysis of GeneChip data for identification of differentials between datasets involve extraction of the probe level data using an unified expression index signifying the estimated level of expression of that transcript summarizing the information in the eleven or more probe-pairs, following normalization or scaling. Some common methods used for this purpose are dCHIP, RMA and MAS (Microarray Suite, currently version 5,0, Affymetrix, CA). The use of unified expression index is advantageous in terms of computational simplicity and easy adaptation of statistical methods to high dimensional datasets. But, due the extremely variable behavior inherent to each probe representing the transcript the unified expression index do not always perform satisfactorily. Consequently, statistical approach to reduction of false positives based on ordered statistics or other Bayesian approaches does not satisfactorily address the issue of false positives. This aspect has recently been evaluated for a few test datasets such as the one used herein. While improvements in the aforementioned aspects are constantly being proposed, statistics applied directly to probe-level data is an attractive alternative. As discussed earlier, several biological and sequence related issues complicate simple selection of a statistical threshold such as a p-value when using the Student's t-test. The following approach is motivated by the fact that the multiple independent features measured signifying the expression level of a transcript should in principle allow selection of a threshold that is appropriate to the noise in a particular data set. In many well behaved dataset this threshold should be lower than a commonly acceptable threshold, e.g., t signifying $p<=0.05$.

Figure 18A:
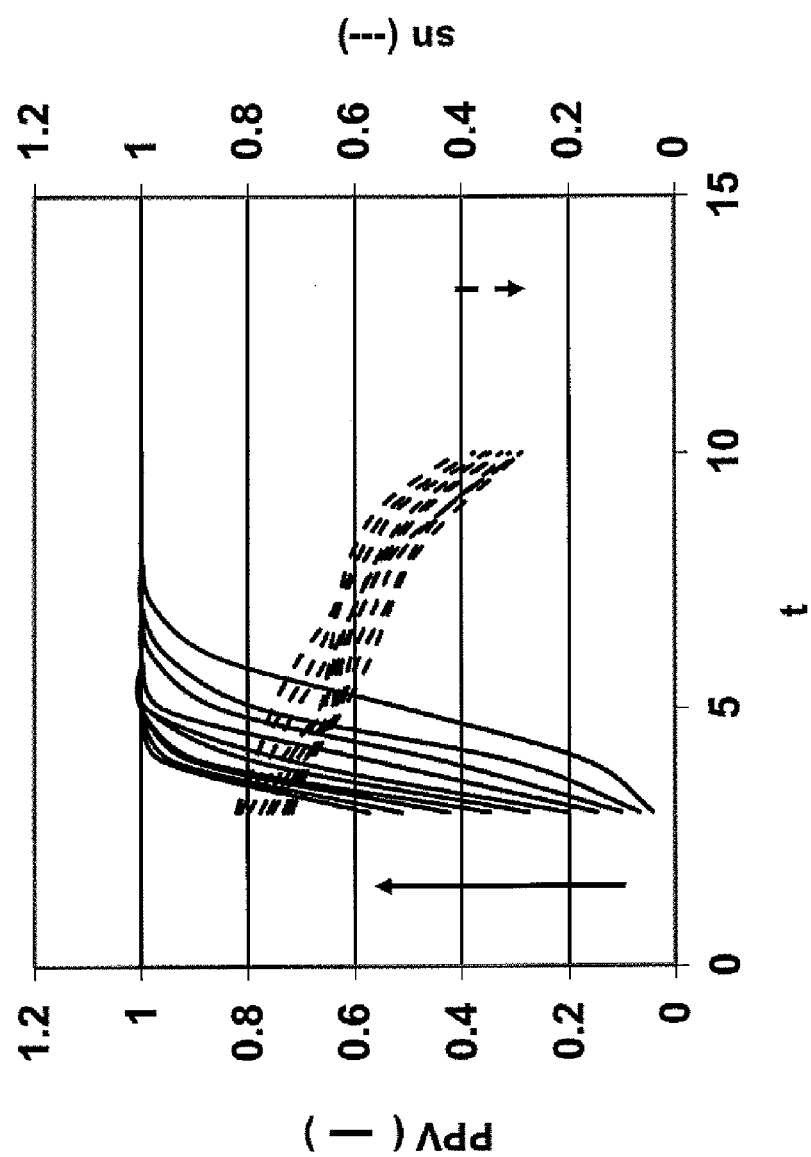
FIGS. 18A, 18B depict effect of parameters on results of interest in one embodiment of the method of these teachings.
Figure 18B:
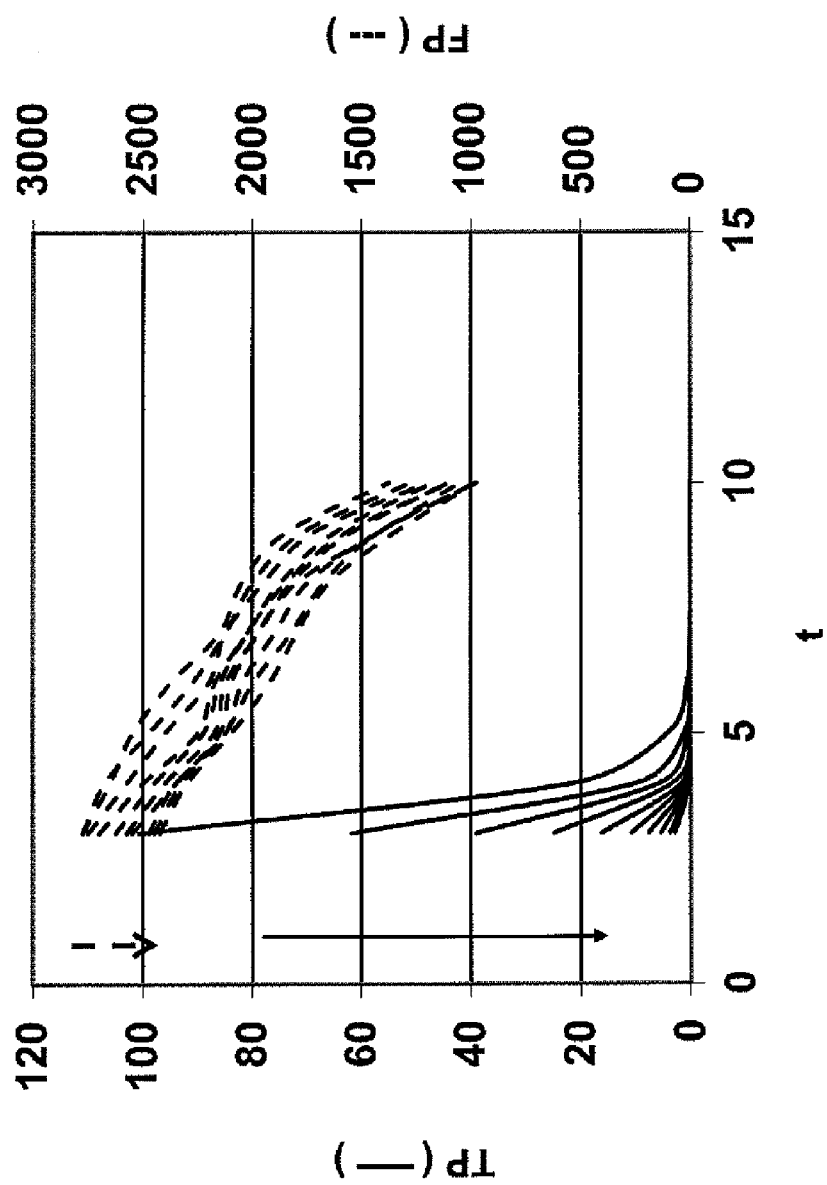

In order to study the performance of differential expression measured at probe level the response surface of sensitivity, positive prediction value, number of true positives and number of false positives were evaluated as a function of number of valid probe-pairs and a range of values for t (the Student's t statistic). This was done with triplicate datasets that had spike-ins of two fold difference with different probesets in concentration ranges (0-512 pM) between the two datasets. A valid probe-pair was defined as one that has a minimum difference of average signal value (difference between signal for perfect match and mismatch) above background, and the ratio of averages is at least 1.1 (selected intuitively, but can be determined empirically for different datasets) and above threshold t, to avoid values in very close range. In addition, a condition that there are no more than one-fifth the probesets that had change in opposite direction was enforced. In general this latter condition was never a determining factor in selec tion of differentials in this dataset. This selection criteria for can be expressed as:

$$\left[\sum_{i=1}^{m}(n\mid t>=t',\,x_{ie}/x_{ib}>=1.1,\,(x_{ie}-x_{ib})>=b)\right]>=np \quad [3]$$

where n is the number of probe-pairs satisfying the conditions, t' is the threshold for t statistic, np is the threshold for number of valid probe-pairs, xie and xib is the signal value for probe-pair i, in experimental and baseline chips, respectively. The above equation represents selection of probesets where the chip designated the experimental chip has higher value than the chip designated the baseline chip, the equation for probesets with value for baseline chip higher can be obtained by interchanging xie and xib. For example for a probeset that satisfies the threshold of 6 valid probe-pairs and t value of 7.0, at least 6 probe-pairs representing that probeset will individually have a t-statistic of 7.0 or above—all having the same direction of change. As can be seen from FIG. 18A, and as expected, with increasing threshold of t and probe-pair threshold the positive prediction value (PPV) increases i.e., a decreasing number of false positives are identified and sensitivity decreases i.e., lesser number of true positives are identified as differentials. FIG. 18B, shows the decrease of true and false positives with increasing threshold of t and np.

The above problem can in principle be viewed as area under the Receiver operating characteristic (ROC) curve problem with two dimensions t threshold as one dimension and number of valid probe-pair number as another dimension. In this kind of situation, one would expect multiple thresholds involving the two dimensions that would have optimal area under the ROC curve. Alternatively, this can be viewed as an optimization problem with the goal of detecting as many true positives with optimal combination sensitivity and positive prediction value. In other words this can be written mathematically as, termed effective number of positives identified (Neff):

$$N_{eff}=TP*TP/(TP+FP)*(1-FP/TP) \quad [4]$$

FIG. 16 shows the response surface of this effective number of positives as a function of t and number of valid probe-pairs (np). It can be seen from the figure that a range of t and np can result in comparable Neff, with top two Neff at (t',np) of (7,5) and (6,6) with (true positives, false positives) of (91,1), (89,1) and (87,0), respectively. The total possible number of true positives and false positives were 135, and 66,555, respectively. It should be noted that the lowest differential (two fold) was used from the dataset, higher differentials would lead to identification of higher number of true positives. The presence of a large portion of the surface across a range of t and np having similar Neff in FIG. 16 suggests that it would be possible to achieve good sensitivity and selectivity for many np and t values thus potentially increasing the sensitivity of detection of small differentials and differentials in transcripts expressed at low levels. This can be achieved in principle by defining a cost factor consisting of the two parameters being tested. One form of defining such a cost adjusted effective number of positives picked (CANeff) would be:

$$CAN_{eff}=N_{eff}/(t'+np) \quad [5]$$

The response surface for CANeff as a function of t' and np is shown in FIG. 17. It can be seen from the surface of CANeff (FIG. 17) that the largely flat area near the peak of Neff (in FIG. 16) can now be reduced to a few distinct and narrow peaks. The (t',np) values yielding the top three CANeff are (3,7), (4,6) and (4,7) with (true positives, false positives) (86, 2), (91,5) and (85,0), respectively. It should be highlighted that these values of true and false positives selected at this threshold are comparable to that of the maximum Neff mentioned before. For comparison, at t signifying p<=0.05 and a threshold of six valid probesets the (true positives,false positives) was (85,0). The number of true and false positives identified and the concentration range of the spike-in positives for a selected set of t' and np values are summarized in Table 1. The possibility of selecting a lower threshold and still being able to maintain high selectivity would especially be of interest (i) with certain datasets where there is a large increase in positives with a small reduction in threshold, whereas the training dataset indicative of variability in the experiment suggest that this would result in a very small number increase in selection of false positives, and (ii) for sensitive identification of small differentials without significant loss of selectivity (illustrated in the next section with some test cases).

Figure 19:
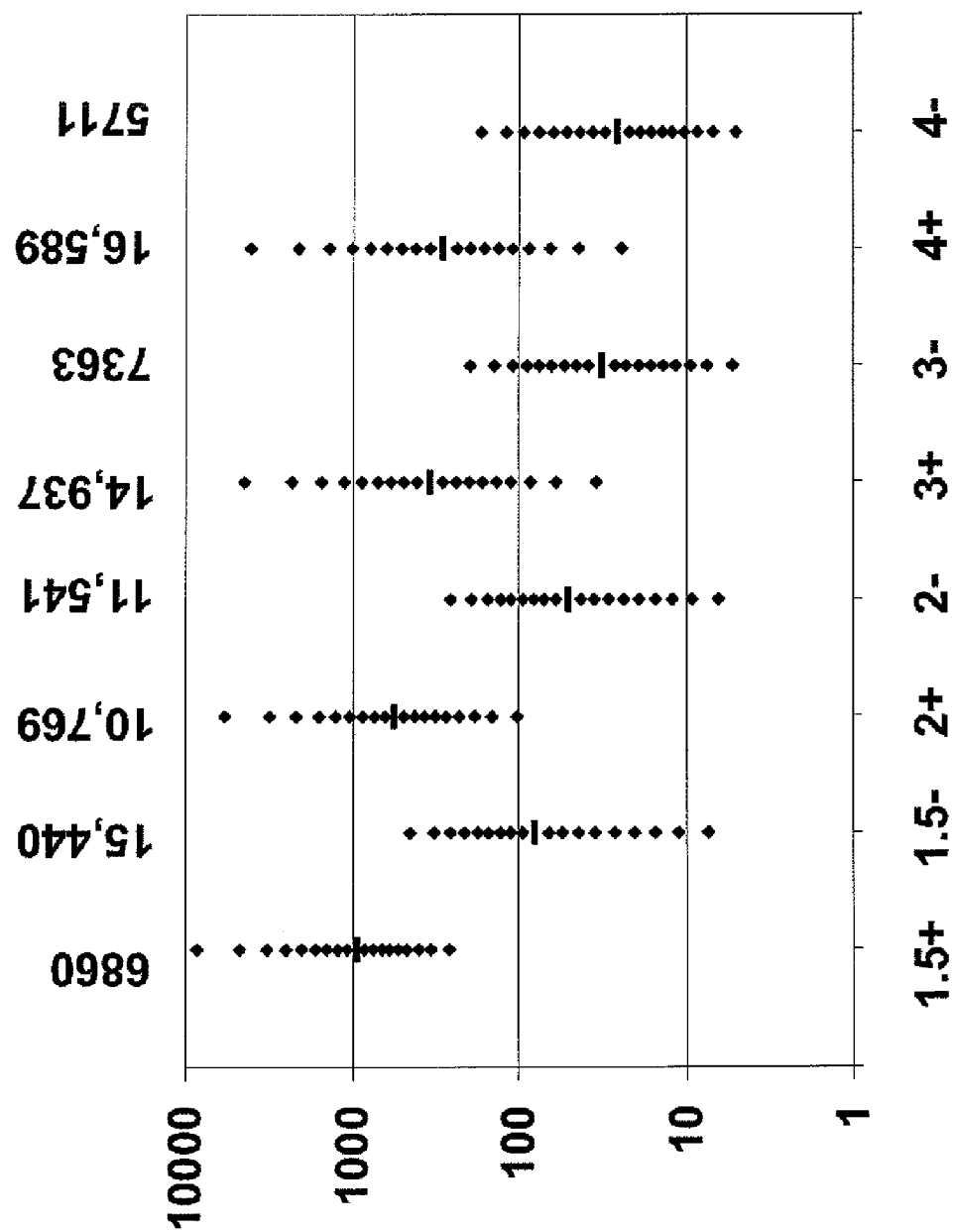
FIG. 19 depicts results of an exemplary embodiment of the method of these teachings.

The methodology outlined above is termed ResurfP, for Response surface assisted Parametric test. It should be noted that lower the threshold that can give good selectivity, the better it is to select small differentials and differentials in transcripts with low expression levels. Thus, the advantage of the lowered threshold were evaluated by scaling one of the two datasets (i.e., the probe level data extracted as outlined herein) used in above comparison to varying extents (1.5, 2, 3 and 4 fold) and comparing to the other dataset. This should allow comparison of data classes with wider variety of variances as opposed to a few signified by the spike-ins. Further, this should also reveal the sensitivity of the methodology in the context of technical replicates, thus revealing the maximum achievable sensitivity. The results for this evaluation at the thresholds yielding the top two CANeff, t signifying p<=0.05, and the threshold specifying the top Neff are represented in Table 2. As expected, the lower thresholds lead to higher sensitivity of detection at any given level. It should be noted that even at the lower threshold (t', np) of (3,6), the differentials (average of three comparisons compared to maximum identifiable differentials defined below) identified were only 42%, 61%, 81% and 86% of 1.5, 2, 3 and 4 fold respectively, which further emphasizes the need for and importance of the proposed approach. At a threshold of (7.71, 6) these values were significantly lower viz., 30%, 47%, 63% and 70%, respectively. For the purpose of calculating percentage of differentials identified the maximum identifiable differentials was set at 21,485, which is the differentials (average of three comparisons) identified at the threshold of (t'=4, np=5) with a scaling factor of 10. A steep decline face on the surface of FIG. 17 (right hand side) with increasing probe-pair threshold together with results indicated in Table 2 also indicate a higher penalty for increasing the probe-pair threshold than for increasing t statistic threshold. Additionally, these data indicate that an appropriate choice of a lower probe-pair threshold can lead to significantly higher number of true differentials without concomitant increase in false positives. In order to have a preliminary characterization of the nature of probesets/transcripts that are selected and are missed in this study, the distribution of the expression indices (to simplify the representation) of these probesets for one of the thresholds (t',np) of (3,7) is shown in FIG. 19. As can be seen from FIG. 19 and as expected the distribution of the expression indices of probesets, low expressors are detected better at higher differential ratios. Conversely, almost all the probesets missed at higher differential ratios were low expressors, which is consistent with observations that there is high variability in the low detection ranges.

The optimal application of ResurfP on biological samples with different properties need additional testing with an independent confirmation using another technology. Nevertheless, the results of a preliminary evaluation to test if the lower threshold identified by ResurfP would lead high false positives when tested on biological replicates are very encouraging. For this purpose (t',np) thresholds of (3,6) and (3,8) were tested on one set of biological replicates from cardiogenomics website (see methods). For this purpose, data from six human patients with aortic stenosis were split into two groups (of triplicates) and the method was evaluated. This lead to identification of only 52 and 21 of 12,624 probesets at (3,6) and (3,8), respectively, even though this chip type consisted of 16 probe-pairs for most probesets/transcripts.

It should be noted that the above exemplary embodiment is presented to better illustrate some of the embodiments of these teachings and does not limit these teachings nor does the above exemplary embodiment illustrate all of the above described embodiments.

The techniques described above may be implemented in one or more computer programs executing on a programmable computer including a processor, a storage medium readable by the processor (including, for example, volatile and non-volatile memory and/or storage, elements), and, in some embodiments, also including at least one input device, and/or at least one output device. Program code may be applied to data entered using the input device (or user interface) to perform the functions described and to generate output information. The output information may be applied to one or more output devices.

Elements and components described herein may be further divided into additional components or joined together to form fewer components for performing the same functions.

Each computer program may be implemented in any programming language, such as assembly language, machine language, a high-level procedural programming language, an object-oriented programming language, or a combination thereof. The programming language may be a compiled or interpreted programming language.

Each computer program may be implemented in a computer program product tangibly embodied in a computer-readable storage device for execution by a computer processor. Method steps of the invention may be performed by a computer processor executing a program tangibly embodied on a computer-readable medium to perform functions of the invention by operating on input and generating output. Other methods and/or computer codes can provide input to these programs based on combinations of components herein or take output from these combinations as input. Combinations of input and output, i.e., communicative and integrative use of components described herein and other methods or computer codes could also be implemented.

Common forms of computer-readable (computer usable) media include, for example, a floppy disk, a flexible disk, hard disk, magnetic tape, or any other magnetic medium, a CDROM, any other optical medium, punched cards, paper tape, any other physical medium with patterns of holes or other patterns, a RAM, a PROM, and EPROM, a FLASH-EPROM, any other memory chip or cartridge, a carrier wave, such as electromagnetic radiation or electrical signals, or any other medium from which a computer can read.

Although the invention has been described with respect to various embodiments, it should be realized this invention is also capable of a wide variety of further and other embodiments within the spirit and scope of the appended claims.

What is claimed is:

1. A computer-implemented method for summarizing parameter value, the method being implemented in a computer and comprising the steps of:
   grouping measurement results from a data set into a plurality of pairs of measurement results;
   determining, for each one pair of measurement results, whether predetermined measures for said each one pair of measurement results satisfy threshold criteria;
   labeling a pair of measurement results from said plurality of pairs of measurement results as not changing if the predetermined measures do not satisfy the threshold criteria;
   comparing, if the predetermined measures satisfied the threshold criteria, one measurement result in said each one pair of measurement results to another measurement result in said each one pair of measurement results;
   classifying, after the comparison, said each one pair of measurement results according to result of the comparison, resulting in a classified plurality of pairs of measurement results;
   selecting a common set of measurement results from the classified plurality of pairs of measurement results for use with the data set; and
   providing summary measures for a parameter utilizing the common set;
   wherein the steps of grouping measurement results, determining whether predetermined measures satisfy threshold criteria, labeling a pair of measurement results, comparing one measurement to another measurement result, classifying according to result of comparison, selecting a common set of measurement results and providing summary measures are performed by a processor executing computer readable code embedded in a non-transitory computer usable medium to perform said steps;
   whereby the data set includes data obtained from large-scale measurements of organismal and cellular state involving multiple independent measurements of each parameter, said parameters including genes, transcripts and proteins; and wherein the summarized parameter values are utilized for decision making to increase confidence on the use of the data in activities including manufacturing of analysis equipment, hybridization of protein, and gene expression.

2. The method of claim 1 further comprising the steps of:
   providing summary measures of predetermined quantities utilizing the common set.

3. The method of claim 2 wherein one of the predetermined quantities is a confidence measure.

4. The method of claim 1 wherein the data set is a replicated data set; and wherein the method further comprises the step of:
   averaging, as a first step, the measurement results over replications to obtain averaged measurement results.

5. The method of claim 4 further comprising the step of: providing summary measures of predetermined quantities utilizing the common set.

6. The method of claim 5 wherein one of the predetermined quantities is a statistical measure.

* * * * *